(12) United States Patent
Power et al.

(10) Patent No.: US 12,048,335 B2
(45) Date of Patent: Jul. 30, 2024

(54) LOWER BODY GARMENTS WITH AN INTERIOR LINING AND RELATED METHODS

(71) Applicant: Knix Wear Inc., Toronto (CA)

(72) Inventors: Julie Power, Toronto (CA); Linda Kritikos, Toronto (CA); Talia Greenberg, Toronto (CA); Christina Greco, Toronto (CA); Joanna Griffiths, Toronto (CA)

(73) Assignee: Knix Wear Inc., Toronto (CA)

( * ) Notice: Subject to any disclaimer, the term of this patent is extended or adjusted under 35 U.S.C. 154(b) by 0 days.

(21) Appl. No.: 17/877,754

(22) Filed: Jul. 29, 2022

(65) Prior Publication Data
US 2024/0032609 A1  Feb. 1, 2024

(51) Int. Cl.
*A41B 9/00* (2006.01)

(52) U.S. Cl.
CPC .................. *A41B 9/004* (2013.01)

(58) Field of Classification Search
CPC ............... A41B 9/004; A61F 13/496
See application file for complete search history.

(56) References Cited

U.S. PATENT DOCUMENTS

| | | |
|---|---|---|
| 2,985,170 A | 5/1961 | Title |
| 3,489,149 A | 1/1970 | Larson |
| 3,608,551 A | 9/1971 | Saburo |
| 3,687,141 A | 8/1972 | Matsuda |
| 4,044,769 A | 8/1977 | Papajohn |
| 4,205,679 A | 6/1980 | Repke et al. |
| 4,352,356 A | 10/1982 | Tong |
| 4,355,425 A | 10/1982 | Jones et al. |
| 4,560,381 A | 12/1985 | Southwell |

(Continued)

FOREIGN PATENT DOCUMENTS

| | | |
|---|---|---|
| AU | 2006209375 A1 | 10/2006 |
| AU | 2014218471 B2 | 10/2016 |

(Continued)

OTHER PUBLICATIONS

English-language machine translation of Japan Patent Application Publication No. JP2005154922, Jun. 16, 2005.

(Continued)

*Primary Examiner* — Richale L Quinn
(74) *Attorney, Agent, or Firm* — Kolitch Romano Dascenzo Gates LLC

(57) ABSTRACT

Lower body garments include a main body having an integral interior lining that is only secured to the main body of the garment around a peripheral lining perimeter of the interior lining. The interior lining may secure a fluid retention gusset such that the outline of the gusset is not visible on outside of garment. A gusset perimeter of the fluid retention gusset may be secured to the interior lining, but not to the main body of the garment, which may result in a leakproof lower body garment that is not immediately recognizable as having such a function when the lower body garment is worn. The interior lining may not extend around the entire right and left leg portions of the main body, such that right and left lateral leg regions may be positioned to separate anterior and posterior portions of the interior lining from each other.

22 Claims, 8 Drawing Sheets

(56) References Cited

U.S. PATENT DOCUMENTS

| | | | |
|---|---|---|---|
| 4,781,962 A | 11/1988 | Zamarripa et al. | |
| 4,813,950 A * | 3/1989 | Branch | A61F 13/49006 |
| | | | 2/401 |
| 4,847,134 A | 7/1989 | Fahrenkrug et al. | |
| 4,898,594 A | 2/1990 | Cottenden | |
| 5,151,092 A | 9/1992 | Buell et al. | |
| 5,167,897 A | 12/1992 | Weber et al. | |
| 5,217,782 A | 6/1993 | Moretz et al. | |
| 5,224,941 A | 7/1993 | Simmons | |
| 5,308,346 A | 5/1994 | Sneller et al. | |
| 5,342,338 A | 8/1994 | Roe | |
| 5,360,420 A | 11/1994 | Cook et al. | |
| 5,368,910 A | 11/1994 | Langdon | |
| 5,411,498 A | 5/1995 | Fahrenkrug et al. | |
| 5,449,352 A | 9/1995 | Nishino et al. | |
| 5,500,270 A | 3/1996 | Langdon et al. | |
| 5,507,895 A | 4/1996 | Suekane | |
| 5,518,801 A | 5/1996 | Chappell et al. | |
| 5,665,452 A | 9/1997 | Langdon et al. | |
| 5,677,028 A | 10/1997 | Ravella | |
| 5,693,169 A | 12/1997 | Langdon et al. | |
| H1732 H | 6/1998 | Johnson | |
| H1746 H | 8/1998 | Carrier et al. | |
| 5,851,204 A | 12/1998 | Mizutani | |
| 5,855,573 A | 1/1999 | Johansson | |
| 5,879,487 A | 3/1999 | Ravella | |
| 5,899,895 A | 5/1999 | Robles et al. | |
| 5,921,974 A * | 7/1999 | Kikuchi | A61F 13/496 |
| | | | 604/385.24 |
| 6,117,523 A | 9/2000 | Sugahara | |
| 6,120,487 A | 9/2000 | Ashton | |
| 6,149,497 A * | 11/2000 | Smith | A61F 5/34 |
| | | | 450/134 |
| 6,174,303 B1 | 1/2001 | Suprise et al. | |
| 6,192,521 B1 * | 2/2001 | Alberts | A61F 13/496 |
| | | | 2/400 |
| 6,231,554 B1 | 5/2001 | Menard | |
| 6,240,569 B1 | 6/2001 | Van Gompel et al. | |
| 6,355,330 B1 | 3/2002 | Koslow et al. | |
| 6,381,994 B1 | 5/2002 | Lee | |
| 6,383,960 B1 | 5/2002 | Everett et al. | |
| 6,569,139 B1 | 5/2003 | Datta et al. | |
| 6,610,901 B2 * | 8/2003 | McMahon-Ayerst | |
| | | | A61F 13/66 |
| | | | 604/378 |
| 6,622,312 B2 | 9/2003 | Rabinowicz | |
| 6,626,883 B2 * | 9/2003 | Wada | A41B 9/004 |
| | | | 604/402 |
| 6,807,685 B1 * | 10/2004 | Hasegawa | A61F 13/505 |
| | | | 2/400 |
| 6,848,121 B1 * | 2/2005 | Halid | A61F 13/66 |
| | | | 2/403 |
| 6,861,520 B1 | 3/2005 | Todd et al. | |
| 7,008,887 B2 | 3/2006 | Rearick et al. | |
| 7,083,604 B2 | 8/2006 | Sakaguchi | |
| 7,156,828 B2 | 1/2007 | Ostrow | |
| RE39,919 E | 11/2007 | Dodge, II et al. | |
| 7,322,966 B1 | 1/2008 | Deerin | |
| 7,393,346 B2 | 7/2008 | Morman et al. | |
| 7,686,794 B2 * | 3/2010 | Mitchell | A61F 13/496 |
| | | | 2/78.3 |
| 7,951,128 B1 * | 5/2011 | Lewis | A61F 13/47236 |
| | | | 604/394 |
| 8,052,665 B2 | 11/2011 | Wastlund-Karlsson et al. | |
| 8,058,343 B2 | 11/2011 | Liu et al. | |
| 8,117,675 B2 | 2/2012 | Strange et al. | |
| 8,282,618 B2 * | 10/2012 | Nordness | A61F 13/496 |
| | | | 604/385.27 |
| 8,460,265 B1 * | 6/2013 | Calender | A61F 13/49006 |
| | | | 604/385.15 |
| D701,018 S * | 3/2014 | Wexler | D2/712 |
| D716,020 S | 10/2014 | Dunbar et al. | |
| 8,935,813 B2 * | 1/2015 | O'Leary | A41B 9/001 |
| | | | 2/400 |
| 9,011,398 B2 | 4/2015 | Johnston et al. | |
| 9,301,551 B2 | 4/2016 | Back et al. | |
| 10,226,388 B2 | 3/2019 | Nelson | |
| 10,335,325 B2 | 7/2019 | Sheldon et al. | |
| 10,441,479 B2 | 10/2019 | Griffiths | |
| 10,441,480 B2 * | 10/2019 | Griffiths | A61F 13/49406 |
| 10,575,573 B2 | 3/2020 | Griffiths | |
| 10,765,564 B2 | 9/2020 | Lee et al. | |
| 10,897,941 B1 * | 1/2021 | Smoter | A41D 31/12 |
| 10,905,596 B2 | 2/2021 | Sina et al. | |
| 11,154,431 B1 * | 10/2021 | Yip | A41B 17/00 |
| 11,207,225 B2 * | 12/2021 | Kajanthan | A61F 13/8405 |
| 11,253,017 B2 * | 2/2022 | Friedrich | A41D 27/13 |
| D948,167 S * | 4/2022 | Carpenter | D2/704 |
| 11,331,229 B2 * | 5/2022 | Lee | A61F 13/496 |
| 11,395,774 B2 * | 7/2022 | Skinner | A61F 13/539 |
| 11,497,263 B1 * | 11/2022 | Deshaies | A41D 31/125 |
| 11,553,739 B2 * | 1/2023 | Henry | A41D 1/08 |
| 11,590,034 B2 | 2/2023 | Deshaies et al. | |
| 11,701,267 B2 | 7/2023 | Greco et al. | |
| 2001/0031957 A1 | 10/2001 | Prestley et al. | |
| 2002/0016580 A1 * | 2/2002 | Wada | A41B 9/12 |
| | | | 604/385.24 |
| 2002/0177829 A1 | 11/2002 | Fell et al. | |
| 2003/0004488 A1 | 1/2003 | Ashton et al. | |
| 2003/0124927 A1 | 7/2003 | Waldroup et al. | |
| 2003/0143376 A1 | 7/2003 | Toyoshima et al. | |
| 2004/0229008 A1 | 11/2004 | Hoying | |
| 2004/0265533 A1 | 12/2004 | Hoying et al. | |
| 2005/0055002 A1 * | 3/2005 | Whitelaw | A61F 13/496 |
| | | | 604/385.03 |
| 2005/0090790 A1 | 4/2005 | Veith | |
| 2005/0131365 A1 | 6/2005 | Sakaguchi | |
| 2005/0197643 A1 * | 9/2005 | Suga | A61F 13/72 |
| | | | 604/396 |
| 2006/0070163 A1 * | 4/2006 | Beck | A41D 27/12 |
| | | | 2/69 |
| 2008/0108962 A1 | 5/2008 | Furuta et al. | |
| 2008/0110775 A1 | 5/2008 | Beck et al. | |
| 2008/0222781 A1 * | 9/2008 | Rhew | A41B 9/04 |
| | | | 604/317 |
| 2008/0275415 A1 | 11/2008 | Wheeler et al. | |
| 2008/0276352 A1 | 11/2008 | Strange et al. | |
| 2009/0240224 A1 | 9/2009 | Underhill et al. | |
| 2009/0247977 A1 | 10/2009 | Takeuchi et al. | |
| 2010/0222759 A1 | 9/2010 | Hammons et al. | |
| 2010/0249736 A1 * | 9/2010 | Png | A41B 17/00 |
| | | | 604/378 |
| 2011/0048077 A1 * | 3/2011 | Warren | A41D 27/245 |
| | | | 66/178 R |
| 2011/0172621 A1 * | 7/2011 | Lee | A61F 13/51 |
| | | | 604/385.03 |
| 2011/0224639 A1 * | 9/2011 | Venable | A61F 13/496 |
| | | | 604/385.01 |
| 2012/0123377 A1 * | 5/2012 | Back | A61F 13/15699 |
| | | | 604/385.01 |
| 2013/0006209 A1 | 1/2013 | Ruiz | |
| 2013/0072888 A1 | 3/2013 | Zorin | |
| 2014/0039432 A1 * | 2/2014 | Dunbar | A61F 13/15577 |
| | | | 604/394 |
| 2014/0378935 A1 | 12/2014 | Arayama et al. | |
| 2016/0089276 A1 * | 3/2016 | Griffiths | A61F 13/532 |
| | | | 604/378 |
| 2016/0184146 A1 * | 6/2016 | Tulk | A01N 37/06 |
| | | | 604/385.15 |
| 2018/0014983 A1 | 1/2018 | Jayasuriya et al. | |
| 2019/0380886 A1 * | 12/2019 | Hammond | A61F 13/49006 |
| 2020/0000155 A1 * | 1/2020 | Etienne | A61F 13/505 |
| 2020/0000649 A1 | 1/2020 | Griffiths | |
| 2020/0154790 A1 | 5/2020 | Cleary | |
| 2020/0222256 A1 * | 7/2020 | Chong | A61F 13/476 |
| 2021/0015684 A1 * | 1/2021 | Nakabugo | A61F 13/49017 |
| 2021/0030605 A1 * | 2/2021 | Kajanthan | A61F 13/4755 |
| 2021/0100698 A1 * | 4/2021 | Langdon | A61F 13/49006 |
| 2021/0177676 A1 * | 6/2021 | Kajanthan | A61F 13/8405 |
| 2021/0282469 A1 * | 9/2021 | Siriwardena | A61F 13/49 |
| 2021/0290447 A1 * | 9/2021 | Sepello | A61F 13/15268 |
| 2021/0298369 A1 * | 9/2021 | Polstein | A41B 9/12 |

(56) References Cited

U.S. PATENT DOCUMENTS

| | | | |
|---|---|---|---|
| 2022/0117790 A1 | 4/2022 | Locke et al. | |
| 2022/0117792 A1 | 4/2022 | Bradford | |
| 2022/0133544 A1 | 5/2022 | Turton et al. | |
| 2022/0160552 A1 | 5/2022 | Carpenter | |
| 2022/0211558 A1 | 7/2022 | Kajanthan et al. | |
| 2022/0249303 A1 | 8/2022 | Yang | |
| 2022/0256938 A1* | 8/2022 | King | A41B 9/12 |
| 2022/0354710 A1* | 11/2022 | Sepello | A61F 13/49446 |
| 2022/0408848 A1* | 12/2022 | Krupa | A61F 13/496 |
| 2023/0010999 A1* | 1/2023 | Sieck | A61F 13/49011 |
| 2023/0128088 A1 | 4/2023 | Deshaies et al. | |

FOREIGN PATENT DOCUMENTS

| | | |
|---|---|---|
| CA | 2126280 | 12/1994 |
| CA | 2126281 | 12/1994 |
| CA | 2152135 | 12/1995 |
| EP | 1370161 | 5/2006 |
| JP | 2005154922 | 6/2005 |
| JP | 2005154924 | 6/2005 |
| KR | 20070018490 | 2/2007 |
| KR | 100694187 | 3/2007 |
| WO | WO 1997046198 | 12/1997 |
| WO | 1998044883 | 10/1998 |
| WO | WO 2006036841 | 4/2006 |
| WO | 2021160627 A1 | 8/2021 |
| WO | 2024012672 A1 | 1/2024 |

OTHER PUBLICATIONS

English-language machine translation of Japan Patent Application Publication No. JP2005154924, Jun. 16, 2005.
English-language machine translation of Korea Patent No. KR100694187, Mar. 6, 2007.
English-language machine translation of Korea Patent Application Publication No. KR20070018490, Feb. 14, 2007.
"Bemis SewFree" webpage (www.bemisheatseal.com/Sewfree.htm), 2 pages, available at least as early as Aug. 4, 2001, retrieved from Internet Archive Wayback Machine (https://web.archive.org/web/20010804041402/http://www.bemisheatseal.com:%2080/Sewfree.htm) on Jan. 29, 2021.
Lo, T.Y., "Techtextil/Avantex 2005 (2)" *Textile Asia*, 2005, pp. 26-27.
Isaacs, Mac, "Seamless: Eliminating Stitches—More Than a Buzzword," *AATCC Review*, Nov. 2005, pp. 16-19.
Swantko, Kathlyn, "Forming A New Bond," *FabricTrends: A GearTrends Supplement*, 2004, pp. 12-14.
Bemis Associates, *Sewfree Adhesive Films for Intimate Apparel*, 2013, 8 pages.
Photographs of Adidas Techfit Period-Proof Biker Short Tights, ordered Jun. 24, 2021.
Photographs Lilova Seamless High Waist, ordered Oct. 12, 2021.
Photographs Lilova Swimwear One-Piece Classic, ordered Oct. 12, 2021.
Photographs of Modibodi Seamfree Bikini Moderate-Heavy, ordered Feb. 9, 2022.
Photographs of Proof Leakproof Hipster Underwear, ordered Aug. 7, 2020.
Photographs of Pure Rosy Banded Brief—Jam, ordered Oct. 12, 2021.
Photographs of Ruby /Love Period Underwear Bikini—Pretty In Pink, ordered May 6, 2021.
Photographs of SPEAX by Thinx Hiphugger Women's Underwear—Leakproof, Breathable—M—Beige, ordered Feb. 7, 2020.
Photographs of TomboyX Leakproof Bikini—Plum, ordered Nov. 10, 2020.
U.S. Appl. No. 17/718,127, filed Apr. 11, 2022, Greco.
U.S. Appl. No. 17/717,986, filed Apr. 11, 2022, Deshaies.
U.S. Appl. No. 63/299,644 to Carlino et al., filed Jan. 14, 2022.
Photographs of Neiwai Pantie Pro Low Waist Period Brief, purchased Dec. 11, 2023.
European Patent Office, Extended European Search Report for related European patent application No. EP23157213, Nov. 23, 2023.

\* cited by examiner

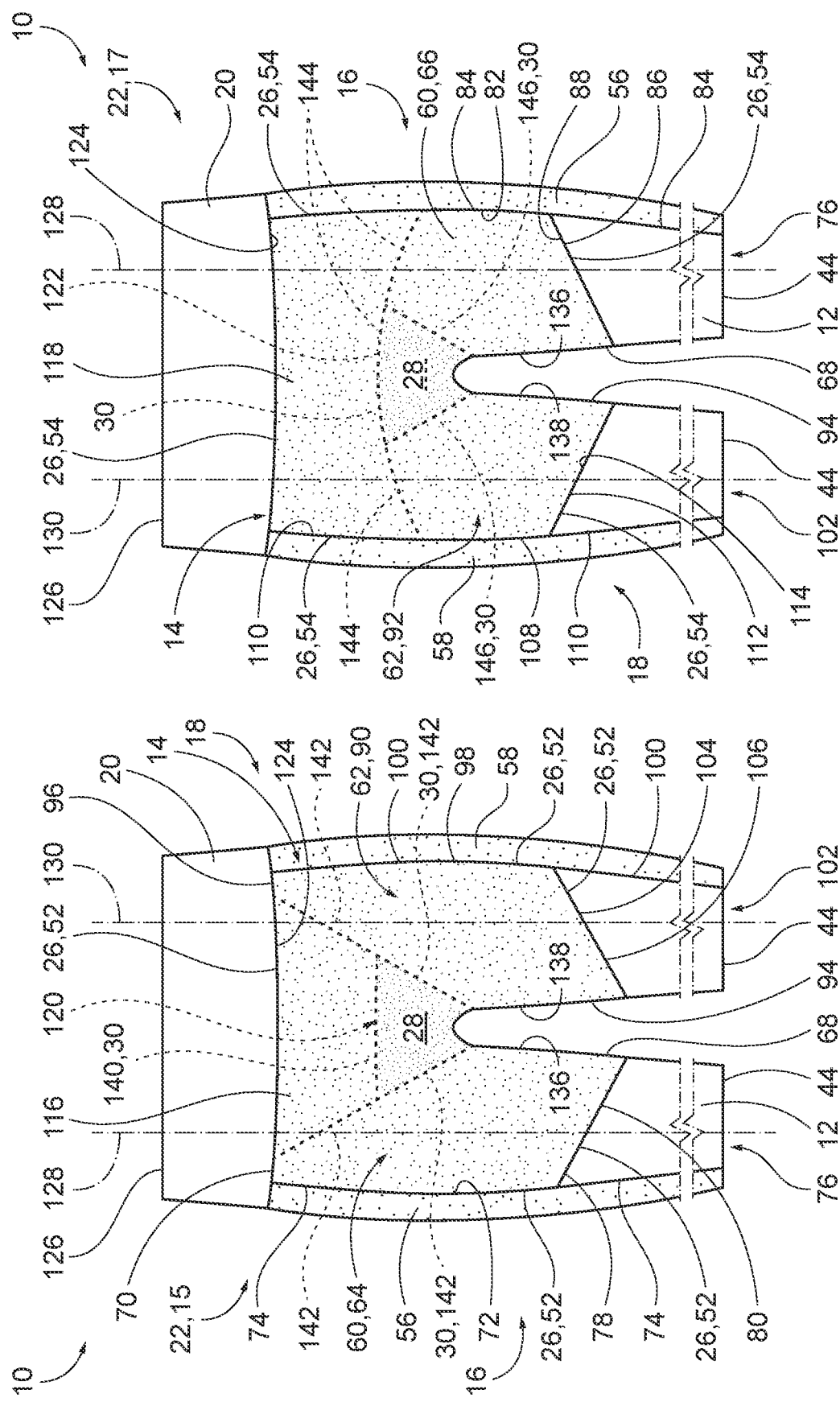

LOWER BODY GARMENTS WITH AN INTERIOR LINING AND RELATED METHODS

FIELD

The present disclosure relates to lower body garments with an interior lining, and related methods.

BACKGROUND

Some types of lower body garments include a liner on the inside of the garment. For example, many types of running shorts or swim trunks include a liner that sometimes functions as built-in underwear. These liners typically are sewn into the inside of the shorts or swim trunks along the waistband, and hang down on the inside of the garment. These liners often include bunched elastic along the leg openings of the liner.

Recently, underwear garments and other wearable accessories that are configured to be worn adjacent to a wearer's crotch, or pelvic region, sometimes include liquid-absorbing properties, such as to absorb and/or retain menstrual fluids, sweat, and/or urine excreted by the user. Wearers generally desire that such garments absorb and retain such fluids in a discreet and leakproof manner, such as to hide such fluids from view by outside observers and/or to enhance the wearer's comfort. These garments may be referred to as "period underwear," or "incontinence underwear." However, many such garments include absorbent regions that are bulky, uncomfortable, and/or difficult to conceal. Additionally conventional attachment of the absorbent regions to the main body of the garment may result in bulkiness, at the expense of the wearer's comfort and the discreetness of the garment, thereby rendering these garments undesirable to be worn as an outer garment and often uncomfortable to be worn under other garments.

To address these considerations, several prior art undergarments include absorbent regions that are bonded and/or laminated to a main body portion of the garment. However, the arrangement of such bonds may be insufficient to fully protect against fluids exiting and/or entering the main body of the garment. Additionally, such constructions may be incompatible with garment applications other than traditional undergarments. There thus remains a need for a lower body garment capable of providing wearers with a discrete leakproof functionality that may be worn as an outer garment, and that is not immediately recognizable by outside observers as providing such functionality.

SUMMARY

Lower body garments according to the present disclosure generally include an integral interior lining that is only secured to the main body of the garment around an outer, or peripheral, perimeter of the interior lining. The interior lining may secure a leakproof gusset with respect to the main body such that the outline of the gusset is not visible on outside of garment.

In an example of presently disclosed lower body garments, the lower body garment includes a main body and an interior lining. The main body includes a right leg portion, a left leg portion, and a waistband portion. The main body further includes an interior side that faces the wearer when the lower body garment is worn, and an exterior side that faces outwardly away from the wearer when the lower body garment is worn. The right leg portion may include a right lateral leg region that is positioned laterally to a first vertically extending centerline of the right leg portion, and similarly, the left leg portion may include a left lateral leg region that is positioned laterally to a second vertically extending centerline of the left leg portion. The interior lining is positioned adjacent the interior side of the main body, and includes a peripheral lining perimeter that is coupled to the main body. The peripheral lining perimeter may include an anterior perimeter portion positioned on an anterior side of the lower body garment, and a posterior perimeter portion positioned on a posterior side of the lower body garment. The right lateral leg region and the left lateral leg region may separate the anterior perimeter portion of the peripheral lining perimeter from the posterior perimeter portion of the peripheral lining perimeter.

In an example of presently disclosed lower body garments, the lower body garment includes a main body, a fluid retention gusset, and an interior lining. The main body includes a right leg portion, a left leg portion, and a waistband portion. The main body also includes an interior side that faces the wearer when the lower body garment is worn and an exterior side that faces outwardly away from the wearer when the lower body garment is worn. The fluid retention gusset may be configured to retain at least 1 teaspoon (5 milliliters (ml)) of fluid excreted from the wearer such that the fluid is at least substantially prevented from exiting the fluid retention gusset to the exterior side of the main body. Such a fluid retention gusset may include a wicking layer, an absorbent layer, and a moisture barrier layer. The wicking layer may be positioned against the wearer when the lower body garment is worn, and the absorbent layer may be configured to absorb and retain at least 1 teaspoon (5 ml) of liquid. The moisture barrier layer may be coupled to the wicking layer such that the absorbent layer is sandwiched between the wicking layer and the moisture barrier layer. The moisture barrier layer may be positioned with respect to the main body such that the moisture barrier layer separates the absorbent layer from the exterior side of the main body. The interior lining may be positioned adjacent the interior side of the main body, and may surround and be coupled to a gusset perimeter of the fluid retention gusset. The interior lining may be configured to secure the fluid retention gusset with respect to the main body such that the fluid retention gusset is not directly coupled to the main body, though the interior lining may include a peripheral lining perimeter that is coupled to the main body.

Related methods are also disclosed. In one method according to the present disclosure, a main body may be formed, and a peripheral lining perimeter of an interior lining may be coupled to the main body. Forming the main body may include forming a main body that has a right leg portion, a left leg portion, a waistband portion, an interior side that faces the wearer when the lower body garment is worn, and an exterior side that faces outwardly away from the wearer when the lower body garment is worn. Forming the main body also may include forming a main body that includes a right lateral leg region of the right leg portion, with the right lateral leg region being positioned lateral to a first vertically extending centerline of the right leg portion. Similarly, forming the main body may include forming a main body that includes a left lateral leg region of the left leg portion, the left lateral leg region being positioned lateral to a second vertically extending centerline of the left leg portion.

Coupling the peripheral lining perimeter of the interior lining to the main body may be performed such that the interior lining is positioned adjacent the interior side of the main body, and such that the right lateral leg region and the left lateral leg region separate an anterior perimeter portion of the peripheral lining perimeter from a posterior perimeter portion of the peripheral lining perimeter. Generally, the anterior perimeter portion is positioned on an anterior side of the lower body garment, and the posterior perimeter portion is positioned on a posterior side of the lower body garment.

BRIEF DESCRIPTION OF THE DRAWINGS

FIG. 4 is a front side elevation view illustrating examples of an interior side of presently disclosed lower body garments.

FIG. 5 is a rear side elevation view illustrating examples of an exterior side of presently disclosed lower body garments.

DESCRIPTION

Figure 1:
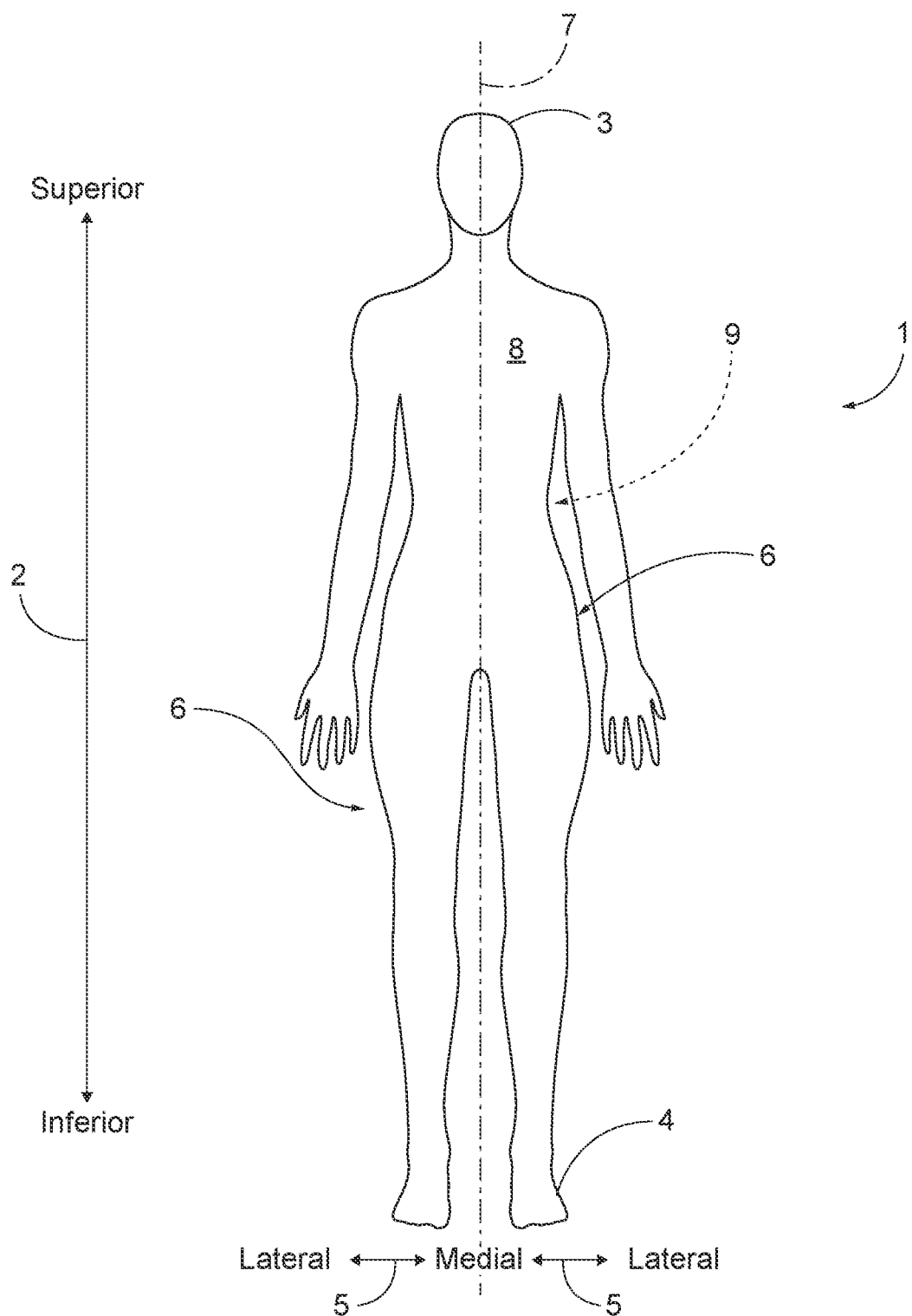
FIG. 1 is a representation of a human figure, providing generic musculature, anatomy, and reference direction indications for use in the specification.

FIG. 1 provides a general reference framework for discussion of presently disclosed lower body garments, with reference to a wearer 1. As indicated by arrow 2, a first component or feature of the disclosed lower body garments may be described as being superior relative to another component or feature, or relative to an aspect of wearer 1, if the first component or feature is closer to the head 3 of wearer 1. Similarly, a first component or feature of the disclosed lower body garments may be described as being inferior relative to another component or feature, or relative to an aspect of wearer 1, if the first component or feature is closer to the feet 4 of wearer 1.

As indicated by arrows 5, a first component or feature of the disclosed lower body garments may be described as being lateral to another component or feature, or to an aspect of wearer 1, if the first component or feature is closer to a side 6 of wearer 1 than is the other component or feature. Likewise, a first component or feature of the disclosed pants garments may be described as being medial to another component or feature, or to an aspect of wearer 1, if the first component or feature is closer to an imaginary centerline 7 of wearer 1 than the other component or feature. Put another way, a first component or feature is medial to a second component or feature if the first component or feature is closer to imaginary centerline 7 than the second component or feature is, whereas a first component or feature is lateral to a second component or feature if the first component or feature is closer to a given side 6 than the second component or feature is. Thus, generally, if a first component or feature is lateral to a second component or feature, then the second component or feature will likewise be medial to the first component or feature.

Components or features of disclosed lower body garments also may be described relative to an anterior side and posterior side of the lower body garments. As used herein, the anterior side of lower body garments refers to the side of the lower body garment that is configured to be positioned on the wearer's anterior side 8 (e.g., the front half of the wearer's body) when the lower body garment is worn. Similarly, the posterior side of lower body garments refers to the side of the lower body garment that is configured to be positioned on the wearer's posterior side 9 (e.g., the back half of the wearer's body).

As represented in FIG. 1 and as described herein, the various elements of lower body garments disclosed herein may be described in terms of relative positions to each other when such lower body garments are worn, or donned, by a wearer, when the wearer is standing vertically, and from the perspective of the wearer. Such terms may include terms such as "above," "below," "upper," "lower," "front," "behind," and similar. Accordingly, when describing a first element as being above or below a second element, the first element falls in a horizontal plane that is above or below a horizontal plane in which the second element falls, but the first element is not necessarily directly above or below the second element along a vertical vector.

Additionally, an "edge" of an element of disclosed lower body garments, as used herein, additionally or alternatively may be referred to as, or described as, an edge region, a margin, or a boundary of the element, and an "edge" is not necessarily the absolute two-dimensional terminus of the element. For example, as typical in garment construction, seams may have a width to them and the region associated with a seam may be considered the edge of the element. Moreover, two panels or sections of material being secured together at a seam often are not perfectly aligned along their terminuses. Moreover, a seam within an expanse of material may define an "edge" of a sub-portion of that expanse of material, with the sub-portion optionally being described as a "panel" or "region" of the material. In other words, two adjacent panels, or regions, may, in some cases, be constructed of the same piece of material with a seam or other structure defining an edge, or boundary, between the two adjacent panels.

FIGS. 2-5 provide illustrative, non-exclusive examples of lower body garments 10, or potential components thereof, according to the present disclosure. Elements that serve a similar, or at least substantially similar, purpose are labeled with like numbers in each of FIGS. 2-5, and these elements may not be discussed in detail herein with reference to each of FIGS. 2-5. Similarly, all elements may not be labeled in each of FIGS. 2-5, but reference numerals associated therewith may be utilized herein for consistency. Elements, components, and/or features that are discussed herein with reference to one or more of FIGS. 2-5 may be included in and/or utilized with any of FIGS. 2-5 without departing from the scope of the present disclosure. In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure.

Figure 2:
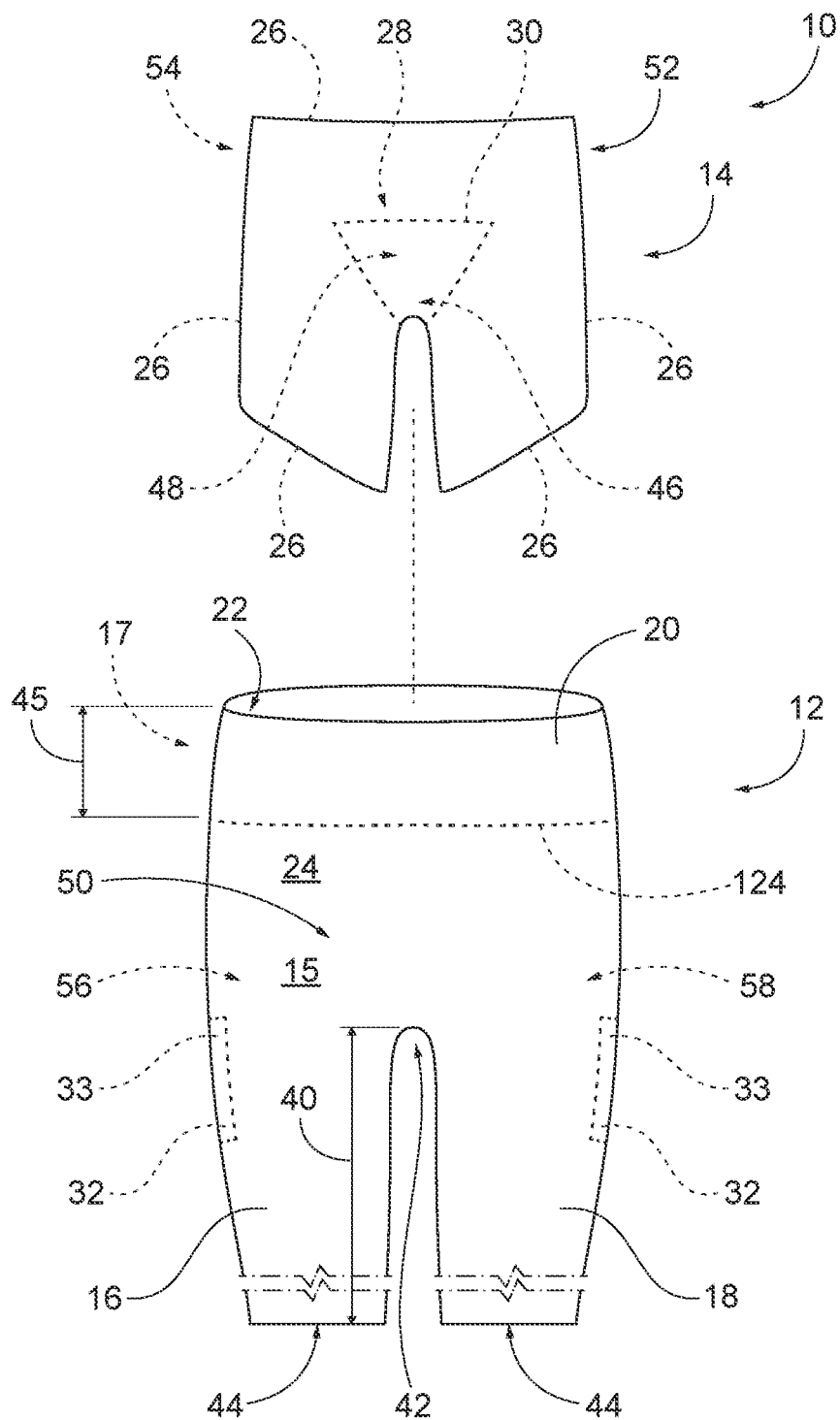
FIG. 2 is an exploded schematic representation of examples of lower body garments according to the present disclosure, shown from the front of the lower body garment.

FIG. 2 schematically represents an exploded view of disclosed lower body garments 10 having a main body 12 and an interior lining 14, viewed from an anterior side 15, or front side, of lower body garment 10. Main body 12 includes a right leg portion 16, a left leg portion 18, and a waistband portion 20. Main body 12 includes an interior side 22 that faces the wearer when lower body garment 10 is worn, and an exterior side 24 that faces outwardly away from the wearer when lower body garment 10 is worn. Interior lining 14 is positioned adjacent interior side 22 of main body 12, such that interior lining 14 is configured to be positioned against the wearer's skin when lower body garment 10 is worn. Interior lining 14 is coupled to main body 12 along a peripheral lining perimeter 26. In some examples, interior lining 14 is only coupled to main body 12 along peripheral lining perimeter 26, and is otherwise not attached to main body 12. This construction has the technical effect of creating a built-in, or integrated interior lining 14 that may be configured to be thin, breathable, and/or stretchable to sit snugly against the wearer's body, without bunching up or being uncomfortable like conventional garments with built-in liners discussed above in the Background section. Because interior lining 14 is secured about peripheral lining perimeter 26, it stays in place and does not have extra fabric that would create bulk, nor does it bunch up while lower body garment 10 is worn. The disclosed construction of interior lining 14 enables other technical benefits as well. For example, interior lining 14 may be coupled to a fluid retention gusset 28, and the disclosed coupling of interior lining 14 to main body 12 may enable interior lining 14 to position fluid retention gusset 28 inside main body 12 without the need for directly coupling fluid retention gusset 28 to main body 12. Fluid retention gusset 28 may be configured to absorb and capture moisture and fluids excreted from the wearer, such that lower body garment 10 may function as a leakproof garment with no visible or present lines or seams on exterior side 24 of lower body garment 10 that would indicate or reveal the presence of fluid retention gusset 28. Disclosed lower body garments 10 may be configured such that any visible seams on exterior side 24 do not give the appearance of a brief or waterproof gusset, and thus disclosed lower body garments 10 may provide improved comfort and discreetness over conventional garments when worn as an outer garment. Instead, external seams on exterior side 24 of lower body garment may coincide with internal seams that secure interior lining along peripheral lining perimeter 26, as will be described in further detail herein. Disclosed lower body garments 10 thus may be configured to reduce or eliminate panty-lines, leaks from fluids such as menstrual blood or urine, and sweat stains. Some examples of lower body garments 10 also may be configured to reduce or eliminate chaffing, via seamless and/or non-bulky construction, and/or to absorb or reduce odor from excreted fluids.

Right leg portion 16 is generally positioned to surround or envelop at least a portion of the wearer's right leg when lower body garment 10 is worn, and left leg portion 18 is generally positioned to surround or envelop at least a portion of the wearer's left leg when lower body garment 10 is worn. Right leg portion 16 and left leg portion 18 may generally extend from respective inferior ends 44 to waistband portion 20. Waistband portion 20, as is well understood in the art, is generally configured to be positioned about the wearer's waist, hips, abdomen, and/or lower torso when lower body garment 10 is worn by the wearer. As right leg portion 16 and left leg portion 18 may extend to waistband portion 20, right leg portion 16 and left leg portion 18 may, in some cases, be positioned on a portion of the wearer's pelvic region and/or lower abdomen or torso, depending on the proportions of lower body garment 10 relative to the proportions of the wearer wearing them. The schematic representation of lower body garments 10 and components and features thereof in FIG. 2 is not intended to represent any exact spacing, proportions, designs, or contours of disclosed lower body garments 10.

In examples of lower body garment 10, peripheral lining perimeter 26 of interior lining 14 may be, or include, a seam that is visible, or present, on both exterior side 24 and interior side 22 of main body 12. In other words, interior lining 14 may be sewn (or otherwise coupled) to main body 12 along peripheral lining perimeter 26, thereby creating a seam present on both sides of the fabric of main body 12 (e.g., exterior side 24 and interior side 22), such that peripheral lining perimeter 26 may be seen from exterior side 24 while lower body garment 10 is worn. Peripheral lining perimeter 26 substantially corresponds to the outer extent, or perimeter, of interior lining 14. Additionally or alternatively to a sewn seam or stitch, interior lining 14 may be secured to main body 12 along peripheral lining perimeter 26 using adhesive or bonding, ultrasonic welding, and/or other means of coupling. In a specific illustrative example, peripheral lining perimeter 26 is secured to main body 12 (thereby coupling interior lining 14 to main body 12) via flatlock stitched seams. Said flatlock stitched seams (or other seams or stitching or attachment) may extend through all fabric layers of main body 12, and may appear as decorative or ornamental seams on exterior side 24 of main body 12. Examples of said ornamental seams are discussed in more detail below in connection with FIGS. 4-5, and may include substantially vertical leg seams on anterior side 15 of main body 12, angled seams on anterior side 15 of main body 12, a waistband seam along an inferior edge seam 124 of waistband portion 20 on anterior side 15 and/or a posterior side 17 of main body 12, and/or vertical and angled leg seams on posterior side 17 of main body 12. On the other hand, interior lining 14 may be sewn, bonded, or otherwise coupled to fluid retention gusset 28 via angled seams along the sides of fluid retention gusset 28 on anterior side 15 and posterior side 17, and/or along top (superior) edges of fluid retention gusset 28, via seams or bonding that do not extend to exterior side 24 of main body 12, such that they are not visible or present when viewing exterior side 24.

Peripheral lining perimeter 26 may be discontinuous between anterior side 15 of lower body garment 10 and the posterior side 17, or back side, of lower body garment 10. For example, peripheral lining perimeter 26 may include an anterior perimeter portion 52 positioned on anterior side 15 of lower body garment 10, and a posterior perimeter portion 54 positioned on posterior side 17 of lower body garment 10. In some examples, anterior perimeter portion 52 may be separated from posterior perimeter portion 54 by a right lateral leg region 56 of right leg portion 16 and a left lateral leg region 58 of left leg portion 18. In some examples, peripheral lining perimeter 26 does not traverse, extend across, underlie, overlap with, coextend to or with, or pass into right lateral leg region 56 or left lateral leg region 58, thereby creating a discontinuity between anterior perimeter portion 52 and posterior perimeter portion 54. In other words, interior lining 14 may be coupled to main body 12 in such a way that interior lining 14 does not extend around the entire circumference of right leg portion 16 or left leg portion 18 (and thus, does not extend around the entire circumference of the wearer's legs while lower body garment 10 is worn). Advantageously, this construction allows some stretch in main body 12 that independent of interior lining 14, and also may be configured to prevent bunching of interior lining 14 by limiting excess material.

As noted above, some examples of interior lining 14 include fluid retention gusset 28, which may be configured to retain at least 1 teaspoon (5 ml) of fluid excreted from the wearer (e.g., urine, blood, sweat, etc.), such that, once captured by fluid retention gusset 28, the fluid is at least substantially prevented from exiting fluid retention gusset 28 to exterior side 24 of main body 12. In examples including fluid retention gusset 28, fluid retention gusset 28 is generally integrated with or into (e.g., sewn to and/or bonded to) interior lining 14. For example, interior lining 14 may surround and be coupled to a gusset perimeter 30 of fluid retention gusset 28. Interior lining 14 may be configured to secure fluid retention gusset 28 with respect to main body 12 such that fluid retention gusset 28 is not directly coupled to main body 12 (and such that interior lining 14 is not directly coupled to main body 12 in the area of fluid retention gusset 28). That said, the coupling of the outer perimeter of interior lining 14 to main body 12 and the coupling of fluid retention gusset 28 to a medial region of interior lining 14, along with the size and shape of interior lining relative to main body 12 and fluid retention gusset 28, may enable interior lining 14 to substantially maintain positioning of fluid retention gusset 28 with respect to the desired anatomical region of the wearer while lower body garment 10 is worn. In other words, while lower body garments 10 advantageously do not require fluid retention gusset 28 to be directly coupled to main body 12, the construction disclosed herein still enables correct positioning of fluid retention gusset 28 with respect to the wearer while lower body garment 10 is worn. Thus, interior lining 14 may be said to be configured to maintain positioning of fluid retention gusset 28 while lower body garment 10 is worn. Fluid retention gusset 28 may be shaped and sized such that it is configured to capture fluids such as blood and urine exiting the wearer's pelvic region while lower body garment 10 is worn. To this end, fluid retention gusset 28 may be sized, shaped, and positioned at least partially within a crotch region 42 and/or a pelvic region 50 of lower body garments 10, such that fluid retention gusset 28 may be positioned adjacent the wearer's crotch or groin area when lower body garment 10 is worn. In some examples, fluid retention gusset 28 may be optimized for different wearers' anatomy and/or may be sized or configured differently for different primary purposes, such as for capturing menstrual blood or for urinary incontinence applications. For example, a fluid retention gusset 28 may be sized, shaped, and/or positioned differently for a urinary incontinence application for wearers with male genitalia than it may be for wearers with female genitalia.

Lower body garment 10 may be configured to absorb and retain any of a variety of fluids, such as may be associated with and/or produced by the wearer while the wearer wears lower body garment 10. For example, lower body garment 10 may be configured to absorb and retain blood and/or other menstrual fluids produced by the wearer, and/or to absorb and retain urine produced by the wearer, such as may be associated with an incontinence condition. However, unlike traditional absorbent garments that include absorbent features that are bulky and/or that are assembled within the garment with bulky stitching, the disclosed construction of lower body garment 10 allows for lower body garment 10 to be low-profile and discreet without compromising the leak-proof properties of the garment.

While peripheral lining perimeter 26 of interior lining 14 may be visibly sewn or otherwise coupled to main body 12, disclosed lower body garments 10 may be provided without visible seams along gusset perimeter 30, such that lower body garments 10 do not visually obviously include said fluid retention gussets 28. To this end, exterior side 24 of main body 12 may be devoid of seams along gusset perimeter 30, as fluid retention gusset 28 is not directly coupled to main body 12 in disclosed lower body garments 10. For example, gusset perimeter 30 may be coupled to interior lining 14 via flatlock stitching that is not attached to main body 12 and not present on exterior side 24 of lower body garment 10. Additionally or alternatively, gusset perimeter 30 may be bonded or otherwise coupled to interior lining 14 without being directly coupled to main body 12. In some examples, a medial, pelvic region 50 of lower body garment 10 is free of seams on exterior side 24, and/or interior lining 14 may not be directly coupled to main body 12 within this medial pelvic region 50 of exterior side 24.

Lower body garments 10 may include one or more pockets 32. As will be shown in more detail in connection with FIGS. 6-8, pockets 32 may include a double pocket formed of at least two partially overlapping pockets 32, may be formed of mesh, and/or may include a closure or be open along the top edge.

Disclosed lower body garments 10 are generally configured to fit tightly or snugly against the wearer's body, and may be any suitable length, such that lower body garments 10 may be provided in the form of shorts, tights, capris, hosiery, skorts, pants, or leggings. Lower body garments 10 may have any desired inseam length, with said inseam length generally corresponding to a distance 40 between crotch region 42 of lower body garment 10 and inferior end 44 of right and left leg portions 16, 18 (e.g., leg openings). In some examples, lower body garment 10 has an inseam length (e.g., distance 40) that is at least 2 inches (5 centimeters (cm)), at least 3 inches (7.5 cm), at least 4 inches (10 cm), at least 5 inches (12.7 cm), at least 6 inches (15.25 cm), at least 7 inches (17.8 cm), at least 8 inches (20 cm), at least 9 inches (22.9 cm), at least 10 inches (25.4 cm), and/or at most 12 inches (30.5 cm), and thus generally corresponds to examples of lower body garments 10 in the form of shorts. In some examples, lower body garments 10 may be provided in the form of shorts having a shorter or longer inseam, and/or may be provided in the form of a brief, or "boyshort" garment. In other examples, lower body garments 10 may have an inseam length (e.g., distance 40) that is at least 15 inches (38 cm), at least 18 inches (45 cm), at least 21 inches (53 cm), at least 24 inches (61 cm), at least 27 inches (68.5 cm), at least 30 inches (76 cm), at least 33 inches (84 cm), and/or at most 36 inches (91 cm), thus generally corresponding to examples of lower body garments 10 in the form of capris, or cropped or full-length tights, leggings, or pants. The disclosed inseam lengths discussed herein are illustrative, and not intended to be limiting, as disclosed lower body garments 10 may be provided in any desirable length including lengths that are shorter or longer than the examples listed herein. In some examples, lower body garments 10 may be provided in the form of athletic tights or shorts. Disclosed lower body garments 10 are generally configured to be worn on their own as an outer garment, though in some examples, lower body garments 10 may be worn as underwear (e.g., athletic underwear) underneath one or more other layers or garments. Further, disclosed lower body garments 10 are not generally intended to be disposable (though the construction disclosed herein may be utilized for disposable garments as well), and may be configured to be machine-washable and re-worn numerous times.

In general, lower body garments 10 and various subcomponents, or elements, thereof, may be constructed of various suitable materials, with illustrative non-exclusive examples including cotton, silk, satin, spandex/elastane, latex, microfiber, lace, polyester, modal, nylon, polybutylene terephthalate (PBT), polyester PBT, polyester spandex blend, cotton-poly-spandex knit, tricot knit, raschel knit, jersey knit, silk and spandex blend, mesh, rayon, jersey, lyocell, tencel, wool, etc., and any suitable combination thereof, which may be used to form the desired materials with the desired characteristics (e.g., stretch, breathability, hand feel, etc.) for the various components of lower body garments 10. Main body 12 may be formed of a fabric that is lightweight, breathable, quick-drying, wicking, stretchable, and/or odor-resistant. In some examples, the material used for main body 12 may have a four-way stretch. Additionally or alternatively, materials selected for main body 12 may provide sun protection (e.g., having an ultraviolet protection factor (UPF) of at least 10, at least 20, at least 30, at least 40, and/or at least 50), be reflective, be cooling, be water-resistant, be wind-resistant, be waterproof, and/or be anti-microbial (and/or features may be added to the material(s) used for main body 12 to impart one or more of these features to lower body garment 10).

In some examples, main body 12 may be formed of a compression knit material, and/or a blended textile, such as a blend of a base textile with spandex/Lycra™ (or other elastic material, such as a bio-based or recycled elastane, Roica™, or Sorona™). In an illustrative example, main body 12 may be formed of nylon and/or elastane. Main body 12 may include a suitable percentage of elastane for a snug, but comfortable, fit on the wearer, such as at least 5% spandex, at least 10% spandex, at least 15% spandex, at least 20% spandex, at least 25% spandex, at least 30% spandex, and/or at least 35% spandex or other stretchable fibers. In a specific, non-limiting example, main body 12 may be formed of a material that is between 75-85% nylon and 15-25% elastane (e.g., 77% nylon and 23% elastane).

Interior lining 14 may be formed of a mesh material, such as a soft stretchable mesh fabric, such as a nylon mesh fabric. Additionally or alternatively, the material selected for interior lining 14 may include cotton, polyester, nylon, and/or spandex. The material selected for interior lining 14 may be breathable, lightweight, thin, and/or non-bunching so as to be comfortable against the wearer's skin. In some examples, the material selected for interior lining 14 may be the same as the material used in main body 12. In some examples, the material used for interior lining 14 may be selected to be warmer and/or aid in body temperature regulation, such as for garments configured for use in colder weather. Due to the materials selected for interior lining 14, the size and shape of interior lining 14, and disclosed methods of coupling interior lining 14 to main body 12 just in some areas, interior lining 14 is configured to create a very different experience for the wearer from conventional sewn-in briefs that look like bunchy underwear hanging on the inside of garments such as conventional swim trunks and running shorts. Instead, interior lining 14 of disclosed lower body garments 10 substantially coincides with interior side 22 of main body 12, such that interior lining 14 lays smoothly against interior side 22 of main body 12 and does not bunch up or provide an extra challenge when donning disclosed lower body garments 10. This may be accomplished via relative sizing and shaping of interior lining 14 with respect to main body 12, as well as via securement of interior lining 14 to main body 12 along peripheral lining perimeter 26. In a sense, interior lining 14 may be said to serve as an inner layer of lower body garment 10, while main body 12 may be said to serve as an outer layer of lower body garment 10, though interior lining 14 is not typically present along the entire interior side 22 of lower body garment. For example, interior lining 14 may be absent within waistband portion 20, within right and left lateral leg regions 56, 58, and/or within right and left leg portions 16, 18 inferior to angled seams 80, 106, 88, and 114 (see FIGS. 7-8). As will be discussed in greater detail herein, interior lining 14 generally is not coupled to (e.g., not sewn or bonded to) main body 12 within pelvic region 50 (e.g., within the wearer's groin area). The coupling of interior lining 14 to main body 12 along peripheral lining perimeter 26, however, generally results in a construction where the space between interior lining 14 and main body 12 is not accessible without damaging the garment or removing the seams or other coupling along peripheral lining perimeter 26. This construction also enables the prevention of bunching of interior lining 14 by securing the material used for interior lining 14 along peripheral lining perimeter 26.

Waistband portion 20 may be seamless in some examples, though in some examples, waistband portion 20 may be sewn or bonded. In some examples of lower body garment 10, waistband portion 20 may include elastic positioned along a superior edge 126 of waistband portion 20 on interior side 22 of lower body garment 10. Said elastic may, for example, be bonded to waistband portion 20 via pin bond mesh glue, bonding tape, silicone bonding glue, and/or pin bond tape, and/or the elastic may be sewn in place within waistband portion 20. In addition to, or instead of, the use of elastic in waistband portion 20, waistband portion 20 may include hook and loop fasteners, buttons, and/or a fly. Additionally or alternatively, a left leg opening 102 at inferior end 44 of left leg portion 18 and/or a right leg opening 76 at inferior end 44 of right leg portion 16 each may include a seamless flocked trim (e.g., SensElast) on interior side 22 of main body 12 to create a seamless construction at leg openings 76, 102.

Lower body garment 10 may, in various examples, be configured to be a high-waisted garment (generally described as "high rise" or "ultra high rise"), a mid-rise garment, or a low-rise garment. In other words, lower body garments 10 may be configured as desired such that waistband portion 20 is positioned at or about the wearer's waist when worn, at or about the wearer's hips when worn, above the wearer's natural waist when worn, below the wearer's natural waist when worn, below the wearer's navel when worn, and/or above the wearer's navel when lower body garment 10 is worn. Waistband portion 20 may have a waistband height 45 that in various examples may be at least 2 inches (5 cm), at least 3 inches (7.6 cm), at least 4 inches (10 cm), at least 5 inches (12.7 cm), at least 6 inches (15 cm), and/or at most 7 inches (18 cm) tall. In some examples, waistband portion 20 may be formed of a single integral piece, or panel, that extends across anterior side 15 and posterior side 17 of lower body garment 10, such that it extends around at least substantially the entire circumference of the wearer's waist, torso, and/or hips. In other examples, waistband portion 20 may be constructed of multiple pieces, or panels, such as a front panel along anterior side 15 of lower body garment 10, and a back panel along posterior side 17 of lower body garment 10. Waistband portion 20 may be constructed of panels and fabrics, without any additional components or features, though in some examples waistband portion 20 optionally may include a drawstring, one or more buttons or other releasable fasteners, one or more belt loops, and/or one or more pockets.

Lower body garments 10 generally are constructed to be pull-on garments, such as leggings or tights, and may be free from zippers, buttons, snaps, or other releasable fasteners to releasably secure waistband portion 20 around the wearer's waist, hips, or torso, though some examples of lower body garments 10 may include one or more of such zippers, buttons, snaps, or other releasable fasteners.

Figure 3:
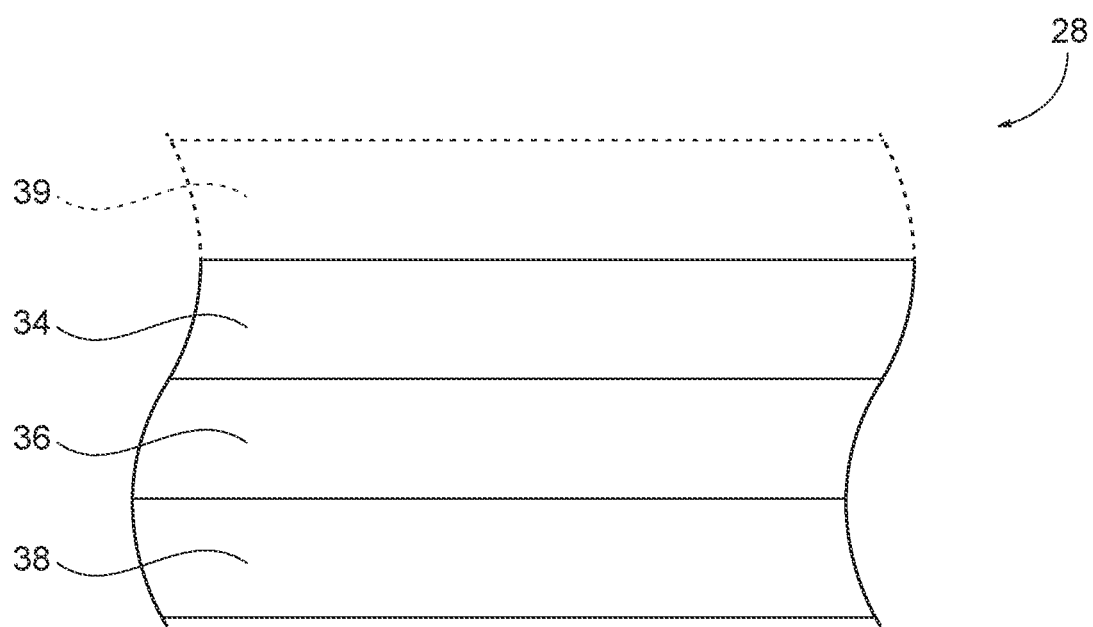
FIG. 3 is a schematic fragmentary cross-sectional side elevation view of examples of a fluid retention gusset that may be included in presently disclosed lower body garments.

With reference to FIG. 3, which schematically illustrates a cross section of an example of fluid retention gusset 28, fluid retention gusset 28 generally includes a plurality of layers of different materials. For example, fluid retention gusset 28 may include a wicking layer 34 (sometimes referred to as a moisture-wicking layer), an absorbent layer 36, and/or a moisture-impermeable layer 38 (sometimes referred to as a moisture barrier, or moisture barrier layer). Wicking layer 34 may be configured to be positioned against the wearer's body when lower body garment 10 is worn and may serve to draw moisture and wick fluids away from the wearer's skin. In particular, in such examples, wicking layer 34 may be configured to draw moisture and fluids away from the wearer, such as via capillary action, and to direct and/or convey the moisture and fluids to one or more absorbent layers 36, though some examples of fluid retention gusset 28 may be provided without wicking layer 34. Absorbent layer 36 may be configured to absorb such moisture and fluids excreted by the wearer, and in some examples is configured to absorb and retain at least 1 teaspoon (5 ml) of liquid. The material and/or thickness of absorbent layer 36 may be varied in different examples to provide different levels of absorbency in fluid retention gusset 28. Additionally or alternatively, absorbent layer 36 may include two or more layers of absorbent materials, which may be the same or different materials. Some examples of lower body garments 10 may be provided without absorbent layer 36, or absorbent layer 36 and moisture-impermeable layer 38 may be combined into a single layer that performs both functions. Moisture-impermeable layer 38 is configured to be water-resistant and/or at least substantially impermeable to liquid and moisture, and sometimes may be referred to as a waterproof, leak-resistant, or leakproof layer. Moisture-impermeable layer 38 may include a leak resistant or waterproof fabric or other moisture barrier material, and/or it may include a moisture barrier layer, film, membrane, treatment, and/or coating. Some examples of fluid retention gusset 28 may include two or more layers or types of moisture barriers, to maximize leak resistance of lower body garments 10 incorporating the same.

The layers of fluid retention gusset 28 are generally coupled together (e.g., via stitching, seams, and/or bonding) and may be substantially coextensive with one another, though in some examples one or more layers may have a slightly larger footprint or area than one or more other layers of fluid retention gusset 28. Moisture impermeable layer 38 may be coupled to wicking layer 34 such that absorbent layer 36 is sandwiched therebetween. Fluid retention gusset 28 may be coupled to interior lining 14 (and interior lining 14 may in turn be coupled to main body 12) such that moisture-impermeable layer 38 is positioned with respect to main body 12 such that moisture-impermeable layer 38 separates absorbent layer 36 from main body 12. In this manner, moisture-impermeable layer 38 may be positioned to prevent fluids absorbed by absorbent layer 36 from contacting or being absorbed by the fabric of main body 12, while wicking layer 34 may be positioned against, or facing, the wearer's skin when lower body garment 10 is worn. Thus, disclosed lower body garments 10 may be configured to be leakproof, via inclusion of said fluid retention gusset 28. Fluid retention gusset 28 may include one or more additional layer or layers, which may be positioned between one or more of layers 34, 36, 38, and/or positioned interiorly to and/or exteriorly to the illustrated example of layers of fluid retention gusset 28. For example, fluid retention gusset 28 may include a top layer 39 of 100% cotton designed to contact the wearer's skin when lower body garment 10 is worn. In other examples, top layer 39 may be omitted, or may be formed of one or more different materials.

While there are many suitable materials for each of the described layers 34, 36, 38 of fluid retention gusset 28, non-limiting examples are disclosed herein. One or more layers 34, 36, 38 of fluid retention gusset 28 may be at least partially formed of a natural fiber, cotton, a synthetic fiber, polyester, nylon, spandex, and/or combinations thereof. In some examples, wicking layer 34 may be formed of, for example, cotton, carbon cotton, and/or carbon cotton spandex. In some examples, wicking layer 34 may be formed of cotton combined with a different material that is configured to improve the performance properties of cotton and/or add additional desired functionality to wicking layer 34. In a non-limiting illustrative example, wicking layer 34 may include 86% cotton, 10% elastane or other elastic fiber, and 4% carbon. Generally, the material for wicking layer 34 may be selected to be quick-drying (in some examples, wicking layer 34 may be configured to dry at least two or three times faster than cotton on its own), configured to prevent or reduce odor, and/or be anti-microbial. In some examples, silver may be embedded into the fibers of the fabric used for wicking layer 34 to impart anti-microbial properties. Absorbent layer 36 may be formed of, for example, polyester nylon, and may be configured to absorb at least at least 1 teaspoon (5 ml), at least 2 teaspoons (10 ml), at least 3 teaspoons (15 ml), at least 4 teaspoons (20 ml), and/or at least 5 teaspoons (25 ml) of fluid(s) excreted by the wearer. Absorbent layer 36 may be surprisingly thin in some examples, so as to avoid creating visible bulk in the pelvic region of lower body garment 10. Moisture-impermeable layer 38 may be formed of, for example, polyester material, a thermoplastic polyurethane laminate (PUL) membrane, a PUL film layer that may or may not be bonded to an additional layer, and/or a fabric with durable water repellency treatment. In some examples, moisture-impermeable layer 38 may be combined with absorbent layer 36 into a single layer that provides both moisture-impermeability and absorption.

As noted, fluid retention gusset 28 may be sized and shaped such that it is configured to be positioned against the wearer's pelvic region when lower body garment 10 is worn, and may be contoured to correspond to the wearer's anatomy. For example, fluid retention gusset 28 may have a varying width along a length of fluid retention gusset 28, such that a first portion 46 of fluid retention gusset 28 is narrower than one or more other portions 48 of fluid retention gusset 28. First portion 46 may be configured to be positioned at the narrowest part of the wearer's pelvic region when lower body garment is worn. While fluid retention gusset 28 may be proportionately adjusted in size as desired for varying applications, absorbency levels, and size of wearers, as an illustrative example, fluid retention gusset 28 may have a length that is at least 6 inches (15 cm), at least 7 inches (17.8 cm), at least 8 inches (20 cm), at least 9 inches (22.8 cm), at least 10 inches (25.4 cm), at least 11 inches (28 cm), at least 12 inches (30.5 cm), at least 13 inches (33 cm), at least 14 inches (35.5 cm), and/or at most 15 inches (38 cm) long. In some examples, fluid retention gusset 28 may have a length that spans the anterior and posterior sides of interior lining 14, or fluid retention gusset 28 may extend just a portion of the length of interior lining 14. Similarly, fluid retention gusset 28 may have a width that spans the width of interior lining 14, or fluid retention gusset 28 may be narrower in width than interior lining 14.

FIGS. 4-5 show a less schematic representation of examples of lower body garment 10, viewed from interior side 22 (e.g., inside out). FIG. 4 shows anterior side 15 of lower body garment 10 (again, viewed from interior side 22), while FIG. 5 shows posterior side 17 of lower body garment 10. Put in general terms, FIG. 4 shows the inside front of an example of lower body garment 10, and FIG. 5 shows the inside back of an example of lower body garment 10, with interior lining 14 shown secured to main body 12 along peripheral lining perimeter 26. In FIGS. 4-5, interior lining 14 is shown in medium density stippling, optional fluid retention gusset 28 is shown in higher density stippling, and right and left lateral leg regions 56, 58 are shown in lower density stippling. Anterior perimeter portion 52 of peripheral lining perimeter 26 is visible in FIG. 4, and posterior perimeter portion 54 of peripheral lining perimeter 26 is visible in FIG. 5.

Interior lining 14 may have a right lining portion 60 and a left lining portion 62. Right lining portion 60 may include a right anterior portion 64 positioned on anterior side 15 of lower body garment 10, and a right posterior portion 66 positioned on posterior side 17 of lower body garment 10. Said portions of interior lining 14 may be separate pieces or panels that are coupled together, or one or more of said portions may be integral with one or more other of said portions. In some examples, right anterior portion 64 joins right posterior portion 66 along a right inseam 68 of lower body garment 10. In some examples, right anterior portion 64 is continuous with right posterior portion 66, with right inseam 68 serving as a convention for discussing different areas of interior lining 14. In other examples, right anterior portion 64 may be a separate piece of fabric that is joined to right posterior portion 66 along right inseam 68 (such variations in potential relationships between respective portions of interior lining 14 may apply to all portions of interior lining discussed herein). Right inseam 68 optionally may include a literal seam or bonding along the wearer's inner thigh, or optionally may simply correspond to a region of lower body garment 10 positioned adjacent the wearer's inner thigh when lower body garment 10 is worn.

In some examples, a right upper edge 70 of right anterior portion 64 joins waistband portion 20 of lower body garment 10. A right lateral edge 72 of right anterior portion 64 may join right lateral leg region 56 of right leg portion 16 of main body 12 along a right anterior vertically extending seam 74, which may be visible and/or present on both interior side 22 and exterior side 24 of main body 12. In some examples, right anterior vertically extending seam 74 extends from waistband portion 20 to or towards right leg opening 76 at inferior end 44 of right leg portion 16. In other words, right anterior vertically extending seam 74 may extend at least substantially all the way to inferior end 44 of right leg portion 16, or right anterior vertically extending seam 74 may extend just a portion of the length of right leg portion 16, such that it ends superior to inferior end 44 of right leg portion 16. In some examples, right anterior vertically extending seam 74 may extend superiorly through some or all of waistband portion 20. Additionally or alternatively, a right lower edge 78 of right anterior portion 64 may extend obliquely between right inseam 68 and right anterior vertically extending seam 74. In some examples, right lower edge 78 of right anterior portion 64 defines a right anterior angled seam 80, which may be present on both interior side 22 and exterior 24 side of main body 12. As discussed in greater detail below, right anterior vertically extending seam 74 and/or right anterior angled seam 80 may at least substantially coincide with a portion of peripheral lining perimeter 26.

With primary reference to FIG. 5, a right lateral edge 82 of right posterior portion 66 may join right lateral leg region 56 of right leg portion 16 of main body 12 along a right posterior vertically extending seam 84, which may be present on both interior side 22 and exterior side 24 of main body 12. Similar to right anterior vertically extending seam 74 (FIG. 4), right posterior vertically extending seam 84 may extend from waistband portion 20 to or towards right leg opening 76 at inferior end 44 of right leg portion 16. In other words, right posterior vertically extending seam 84 may extend at least substantially all the way to inferior end 44 of right leg portion 16, or right posterior vertically extending seam 84 may extend just a portion of the length of right leg portion 16, such that it ends superior to inferior end 44 of right leg portion 16. In some examples, right posterior vertically extending seam 84 may extend superiorly through some or all of waistband portion 20. Additionally or alternatively, a right lower edge 86 of right posterior portion 66 may extend obliquely between right inseam 68 and right posterior vertically extending seam 84. In some examples, right lower edge 86 of right posterior portion 66 defines a right posterior angled seam 88, which may be present on both interior side 22 and exterior side 24 of main body 12. As discussed in greater detail below, right posterior vertically extending seam 84 and/or right posterior angled seam 88 may at least substantially coincide with a portion of peripheral lining perimeter 26.

Similarly, and with reference to both FIGS. 4 and 5, left lining portion 62 may include a left anterior portion 90 positioned on anterior side 15 of lower body garment 10, and a left posterior portion 92 positioned on posterior side 17 of lower body garment 10. In some examples, left anterior portion 90 joins left posterior portion 92 along a left inseam 94 of lower body garment 10. Left inseam 94 optionally may include a literal seam along the wearer's inner thigh, or optionally may simply correspond to a region of lower body garment 10 positioned adjacent the wearer's inner thigh when lower body garment 10 is worn. In some examples, a left upper edge 96 of left anterior portion 90 joins waistband portion 20 of lower body garment 10. A left lateral edge 98 of left anterior portion 90 may join left lateral leg region 58 of left leg portion 18 of main body 12 along a left anterior vertically extending seam 100, which may be visible and/or present on both interior side 22 and exterior side 24 of main body 12. In some examples, left anterior vertically extending seam 100 extends from waistband portion 20 to or towards a left leg opening 102 at inferior end 44 of left leg portion 18. In other words, left anterior vertically extending seam 100 may extend at least substantially all the way to inferior end 44 of left leg portion 18, or left anterior vertically extending seam 100 may extend just a portion of the length of left leg portion 18, such that it ends superior to inferior end 44 of left leg portion 18. In some examples, left anterior vertically extending seam 100 may extend superiorly through some or all of waistband portion 20. Additionally or alternatively, a left lower edge 104 of left anterior portion 90 may extend obliquely between left inseam 94 and left anterior vertically extending seam 100. In some examples, left lower edge 104 of left anterior portion 90 defines a left anterior angled seam 106, which may be present on both interior side 22 and exterior 24 side of main body 12. As discussed in greater detail below, left anterior vertically extending seam 100 and/or left anterior angled seam 106 may at least substantially coincide with a portion of peripheral lining perimeter 26.

With primary reference to FIG. 5, a left lateral edge 108 of left posterior portion 92 may join left lateral leg region 58 of left leg portion 18 of main body 12 along a left posterior vertically extending seam 110, which may be present on both interior side 22 and exterior side 24 of main body 12. Similar to left anterior vertically extending seam 100 (FIG. 4), left posterior vertically extending seam 110 may extend from waistband portion 20 to or towards left leg opening 102 at inferior end 44 of left leg portion 18. In other words, left posterior vertically extending seam 110 may extend at least substantially all the way to inferior end 44 of left leg portion 18, or left posterior vertically extending seam 110 may extend just a portion of the length of left leg portion 18, such that it ends superior to inferior end 44 of left leg portion 18. In some examples, left posterior vertically extending seam 110 may extend superiorly through some or all of waistband portion 20. Additionally or alternatively, a left lower edge 112 of left posterior portion 92 may extend obliquely between left inseam 94 and left posterior vertically extending seam 110. In some examples, left lower edge 112 of left posterior portion 92 defines a left posterior angled seam 114, which may be present on both interior side 22 and exterior side 24 of main body 12. As discussed in greater detail below, left posterior vertically extending seam 110 and/or left posterior angled seam 114 may at least substantially coincide with a portion of peripheral lining perimeter 26.

Right leg portion 16 includes right lateral leg region 56, and left leg portion 18 includes left lateral leg region 58. Left lateral leg region 58 may extend between left anterior vertically extending seam 100 and left posterior vertically extending seam 110. Additionally or alternatively, right lateral leg region 56 may extend between right anterior vertically extending seam 74 and right posterior vertically extending seam 84. Thus, right and left lateral leg regions 56, 58 are generally positioned on the respective lateral portions of right and left leg portion 16, 18. In some examples, right and left lateral leg regions 56, 58 extend inferiorly from waistband portion 20 (e.g., from inferior edge seam 124 of waistband portion 20). In some examples, right and left lateral leg regions 56, 58 may extend superiorly through some or all of waistband portion 20. In some examples, right and left lateral leg regions 56, 58 extend inferiorly substantially along the entire length of right and left leg portions 16, 18, respectively, while in other examples, right and left lateral leg regions 56, 58 may extend along just a portion of the length of right and left leg portions 16, 18, respectively, such that they end superior to inferior ends 44 of right and left leg portions 16, 18. In some examples, right and left lateral leg regions 56, 58 may be at least substantially devoid of seams passing through or traversing the lateral leg regions. Further, in some examples, interior lining 14 is not coupled to right and left lateral leg regions 56, 58, except along vertically extending seams 74, 84, 100, 110. Thus, right lateral leg region 56 may serve to separate right anterior portion 64 of interior lining 14 from right posterior portion 66 of interior lining 14. Similarly, left lateral leg region 58 may serve to separate left anterior portion 90 of interior lining 14 from left posterior portion 92 of interior lining 14. Put another way, interior lining 14 does not extend around the entire right leg portion 16 or left leg portion 18 because interior lining 14 does not coextend across or traverse the right and left lateral leg regions 56, 58. Put yet another way, peripheral lining perimeter 26 of interior lining 14 is said to be discontinuous because anterior perimeter portion 52 of peripheral lining perimeter 26 is separated from posterior perimeter portion 54 by right and left lateral leg regions 56, 58.

Right lateral leg region 56 thus may be said to be bounded on anterior side 15 of lower body garment 10 by right anterior vertically extending seam 74, and right lateral leg region 56 may be said to be bounded on posterior side 17 of lower body garment 10 by right posterior vertically extending seam 84. Similarly, left lateral leg region 58 may be said to be bounded on anterior side 15 of lower body garment 10 by left anterior vertically extending seam 100, and left lateral leg region 58 may be said to be bounded on posterior side 17 of lower body garment 10 by left posterior vertically extending seam 110. Right lateral leg region 56 is positioned laterally to a first vertically extending centerline 128 of right leg portion 16, while left lateral leg region 58 is positioned laterally to a second vertically extending centerline 130 of left leg portion 18. In some examples, right lateral leg region 56 may be a separate piece of fabric or panel that is coupled to the rest of main body 12 along right anterior vertically extending seam 74 and right posterior vertically extending seam 84. Similarly, left lateral leg region 58 may be a separate piece of fabric or panel that is coupled to the rest of main body 12 along left anterior vertically extending seam 100 and left posterior vertically extending seam 110. In some examples, right lateral leg region 56 and/or left lateral leg region 58 may be continuous with adjacent portions of main body 12. For example, right lateral leg region 56 may be continuous with portions of main body 12 that overlie right anterior portion 64 and right posterior portion 66 of interior lining 14, and left lateral leg region 58 may be continuous with portions of main body 12 that overlie left anterior portion 90 and left posterior portion 92 of interior lining. In such examples, vertically extending seams 74, 84, 100, 110 may simply correspond to the locations where interior lining 14 is sewn or otherwise coupled to main body 12.

With continued reference to FIGS. 4-5, interior lining 14 may include a superior anterior portion 116 (FIG. 4) and/or a superior posterior portion 118 (FIG. 5). In some examples, superior anterior portion 116 joins waistband portion 20, an anterior superior edge 120 of fluid retention gusset 28, right anterior portion 64 of interior lining 14, and left anterior portion 90 of interior lining 14. Additionally or alternatively, superior anterior portion 116 may extend laterally to at least partially underlie both right leg portion 16 and left leg portion 18. While some examples of lower body garments 10 include superior anterior portion 116, in other examples, fluid retention gusset 28 may extend superiorly further towards waistband portion 20 such that superior anterior portion 116 is smaller than the example of FIG. 4, or lower body garment 10 may be provided without superior anterior portion 116 (e.g., fluid retention gusset 28 may extend superiorly to waistband portion 20 and/or may extend laterally to or further towards right anterior vertically extending seam 74 and/or left anterior vertically extending seam 100 than is shown in FIG. 4).

As shown in FIG. 4, interior lining 14 may include an anterior laterally extending seam 140 along anterior superior edge 120. In some examples, anterior laterally extending seam 140 is not coupled to main body 12. Anterior laterally extending seam 140 may serve to help couple fluid retention gusset 28 to interior lining 14. In other words, anterior laterally extending seam 140 may form a portion of gusset perimeter 30, with fluid retention gusset 28 being coupled to interior lining 14 along gusset perimeter 30 (though gusset perimeter 30 is not coupled to main body 12 in preferred examples, and thus is not present on exterior side 24). Anterior laterally extending seam 140 may be formed of flatlock stitching, or other low profile or minimally visible stitching or bonding technique. Anterior laterally extending seam 140 is shown as being substantially straight (i.e., horizontal) in FIG. 4, though in various examples of lower body garments 10, anterior laterally extending seam 140 may be curved, such as having a slight upward or downward curved shape. Anterior laterally extending seam 140 may extend laterally between two anterior obliquely-extending seams 142. In various examples, anterior laterally extending seam 140 may intersect, traverse, be bounded by, and/or extend at least substantially to meet one or both anterior obliquely-extending seams 142.

Anterior obliquely-extending seams 142 may form a portion of gusset perimeter 30 along the sides of fluid retention gusset 28, such that anterior obliquely-extending seams 142 may serve to couple a portion of fluid retention gusset 28 to interior lining 14. In some examples, anterior obliquely-extending seams 142 may extend along interior lining 14, continuing superior to fluid retention gusset 28. For example, anterior obliquely-extending seams 142 may extend superiorly to waistband portion 20 (e.g., to inferior edge seam 124). Anterior obliquely-extending seams 142 are not coupled to main body 12 in preferred examples of lower body garments 10, and thus are not present on exterior side 24. Anterior obliquely-extending seams 142 are illustrated as being substantially straight angled seams in FIG. 4, though may have a slight curved shape, such as in areas where fluid retention gusset 28 is narrower, which may improve fit and comfort for wearers. Anterior obliquely-extending seams 142 may be formed of flatlock stitching, or other low profile or minimally visible stitching or bonding technique.

Similarly, and with reference to FIG. 5, in some examples, superior posterior portion 118 joins waistband portion 20, a posterior superior edge 122 of fluid retention gusset 28, right posterior portion 66 of interior lining 14, and left posterior portion 92 of interior lining 14. Additionally or alternatively, superior posterior portion 118 may extend laterally to at least partially underlie both right leg portion 16 and left leg portion 18. Additionally or alternatively, superior posterior portion 118 may join right posterior vertically extending seam 84 and left posterior vertically extending seam 110, as shown in FIG. 5. While some examples of lower body garments 10 include superior posterior portion 118, in other examples, fluid retention gusset 28 may extend superiorly further towards waistband portion 20 such that superior posterior portion 118 is smaller than the example of FIG. 5, or lower body garment 10 may be provided without superior posterior portion 118 (e.g., fluid retention gusset 28 may extend superiorly to waistband portion 20 and/or may extend laterally to or further towards right posterior vertically extending seam 84 and/or left posterior vertically extending seam 110 than is shown in FIG. 5). Interior lining 14 may include a posterior laterally extending seam 144 along posterior superior edge 122 of fluid retention gusset 28.

In some examples, posterior laterally extending seam 144 is not coupled to main body 12, and thus is not present on exterior side 24. Posterior laterally extending seam 144 may serve to help couple fluid retention gusset 28 to interior lining 14. In other words, posterior laterally extending seam 144 may form a portion of gusset perimeter 30, with fluid retention gusset 28 being coupled to interior lining 14 along gusset perimeter 30 (though gusset perimeter 30 is not coupled to main body 12 in preferred examples). Posterior laterally extending seam 144 may be formed of flatlock stitching, or other low profile or minimally visible stitching or bonding technique. Posterior laterally extending seam 144 may be curved in some examples. For example, the example of lower body garment 10 shown in FIG. 5 has a posterior laterally extending seam 144 with a slight downward curved shape to it, though this configuration is not limiting. In other examples, posterior laterally extending seam 144 may be substantially straight, may be an upward curved shape to it, may be undulating, or have any other desired contour line or shape. Posterior laterally extending seam 144 may extend laterally from right posterior vertically extending seam 84 to left posterior vertically extending seam 110 in some examples. In other examples, posterior laterally extending seam 144 may extend just a portion across interior lining 14. For example, posterior laterally extending seam 144 may intersect or be bounded by two posterior obliquely-extending seams 146. Posterior obliquely-extending seams 146 may form a portion of gusset perimeter 30 along the sides of fluid retention gusset 28, such that posterior obliquely-extending seams 146 may serve to couple a portion of fluid retention gusset 28 to interior lining 14. In some examples, posterior obliquely-extending seams 146 may extend along interior lining 14, continuing superior to fluid retention gusset 28. For example, posterior obliquely-extending seams 146 may extend superiorly to meet waistband portion 20 (e.g., to inferior edge seam 124), though in the example shown in FIG. 5, posterior obliquely-extending seams 146 only extend superiorly to meet, or intersect with posterior laterally extending seam 144 (i.e., posterior obliquely-extending seams 146 do not extend all the way to waistband portion 20 in the example of FIG. 5, though they may extend further in other examples of lower body garments 10). In other words, while the example of FIG. 5 shows posterior obliquely-extending seams 146 stopping where they meet posterior laterally extending seam 144, in other examples, posterior obliquely-extending seams 146 may continue past posterior laterally extending seam 144. Posterior obliquely-extending seams 146 are not coupled to main body 12 in preferred examples of lower body garments, and thus are not present on exterior side 24. Posterior obliquely-extending seams 146 may be formed of flatlock stitching, or other low profile or minimally visible stitching or bonding technique. In some examples, posterior obliquely-extending seams 146 may be continuous with anterior obliquely-extending seams 142. In other words, anterior obliquely-extending seams 142 may continue along gusset perimeter 30 from anterior side 15, along the wearer's groin region, all the way to posterior side 17, thereby becoming posterior obliquely-extending seams 146.

While FIGS. 4-5 illustrate fluid retention gusset 28 as being spaced away from peripheral lining perimeter 26, in some examples, fluid retention gusset 28 may be larger than shown in these examples. For example, one or more portions of gusset perimeter 30 may coincide with one or more portions of peripheral lining perimeter 26, such that fluid retention gusset 28 could be as long and/or as wide as interior lining 14 in some areas of some examples of lower body garments 10. In some examples, fluid retention gusset 28 may be proportionately larger, such that gusset perimeter 30 is positioned relatively closer to peripheral lining perimeter 26 than shown in the examples of FIGS. 4-5. In yet other examples, lower body garments 10 with interior linings 14 may be provided without fluid retention gusset 28 at all.

With reference to FIGS. 4-5, interior lining 14 may include one or more additional seams that are not coupled to main body 12 in some examples. For example, interior lining 14 may include a right lining inseam 136 and/or a left lining inseam 138. In some examples, right lining inseam 136 and left lining inseam 138 are not coupled to main body 12. In other words, right lining inseam 136 may be free from coupling to right inseam 68 of main body 12, and/or left lining inseam 138 may be free from coupling to left inseam 94 of main body 12. In other examples of lower body garment 10, right lining inseam 136 may be coupled to main body 12 (e.g., to right inseam 68) and/or left lining inseam 138 may be coupled to main body 12 (e.g., to left inseam 94). When right lining inseam 136 and left lining inseam 138 are not coupled to main body 12, they are generally not present (and thus not visible) on exterior side 24. Right lining inseam 136 and left lining inseam 138 may be formed of flatlock stitching, or other low profile or minimally visible stitching or bonding technique.

In some examples, peripheral lining perimeter 26 is at least partly defined by and/or coincides with right upper edge 70 of right anterior portion 64 of interior lining 14, left upper edge 96 of left anterior portion 90 of interior lining 14, at least part of right anterior vertically extending seam 74, at least part of left anterior vertically extending seam 100, at least part of right posterior vertically extending seam 84, at least part of left posterior vertically extending seam 110, left posterior angled seam 114, left anterior angled seam 106, right anterior angled seam 80, and/or right posterior angled seam 88. Additionally or alternatively, peripheral lining perimeter 26 may be partly defined by and/or coincide with inferior edge seam 124 of waistband portion 20 along anterior side 15 of lower body garment 10 and/or along posterior side 17 of lower body garment 10. In this manner, peripheral lining perimeter 26 of interior lining 14 may coincide with the seams that are visible on exterior side 24 of lower body garment 10 (see FIG. 7), while maintaining an aesthetic appearance on exterior side 24 that does not appear to look like briefs or a gusset. In other words, interior lining 14 may be coupled to main body 12 along peripheral lining perimeter 26 to create a discrete functionality for lower body garments 10 such that peripheral lining perimeter 26 may be configured to simply appear to be aesthetic design elements of lower body garment 10, rather than being outwardly apparent that the garment may have a gusset or leakproof functionality.

Figure 6:
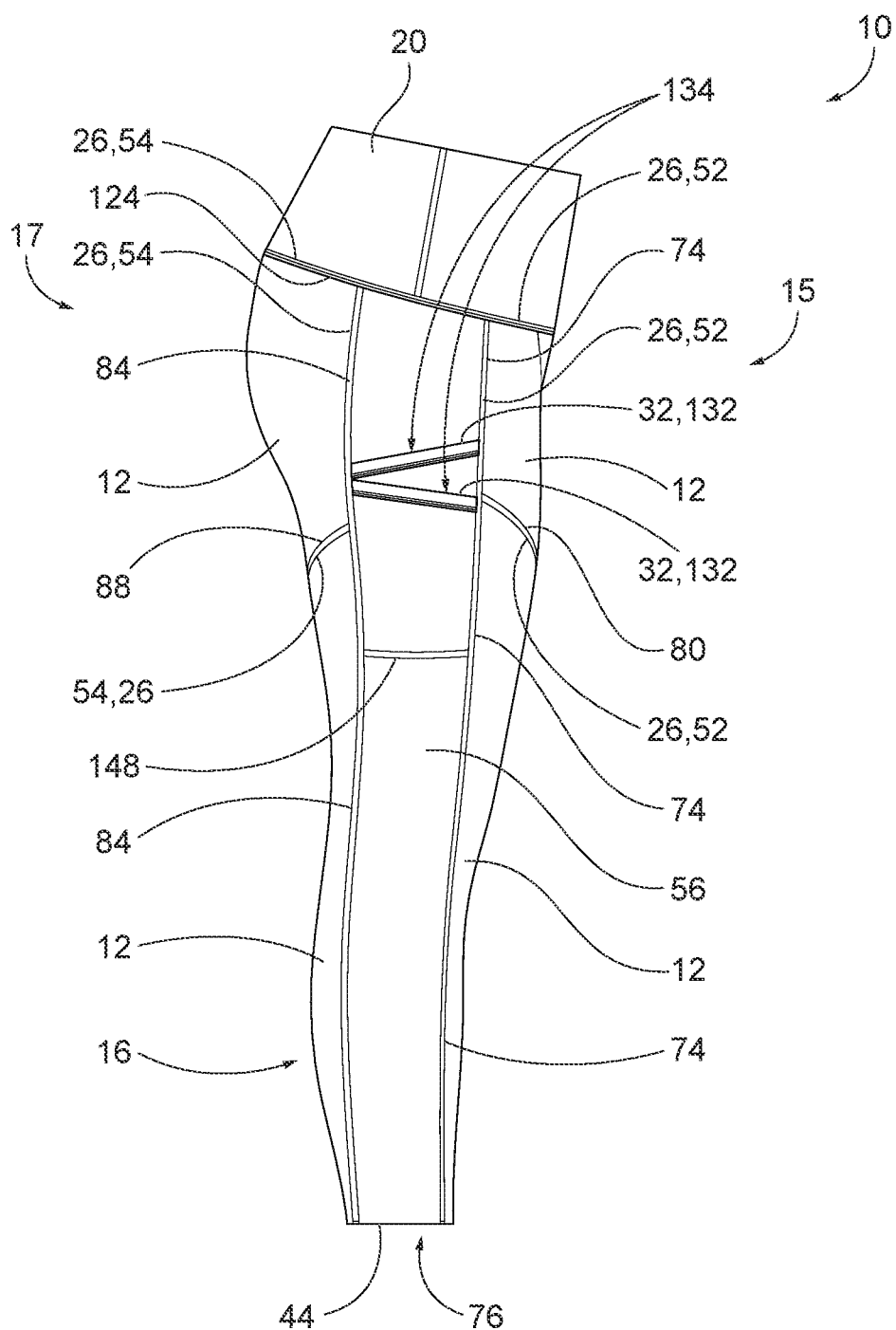
FIG. 6 is a side elevation view of an example of presently disclosed lower body garments, shown in an as-worn configuration.
Figure 7:
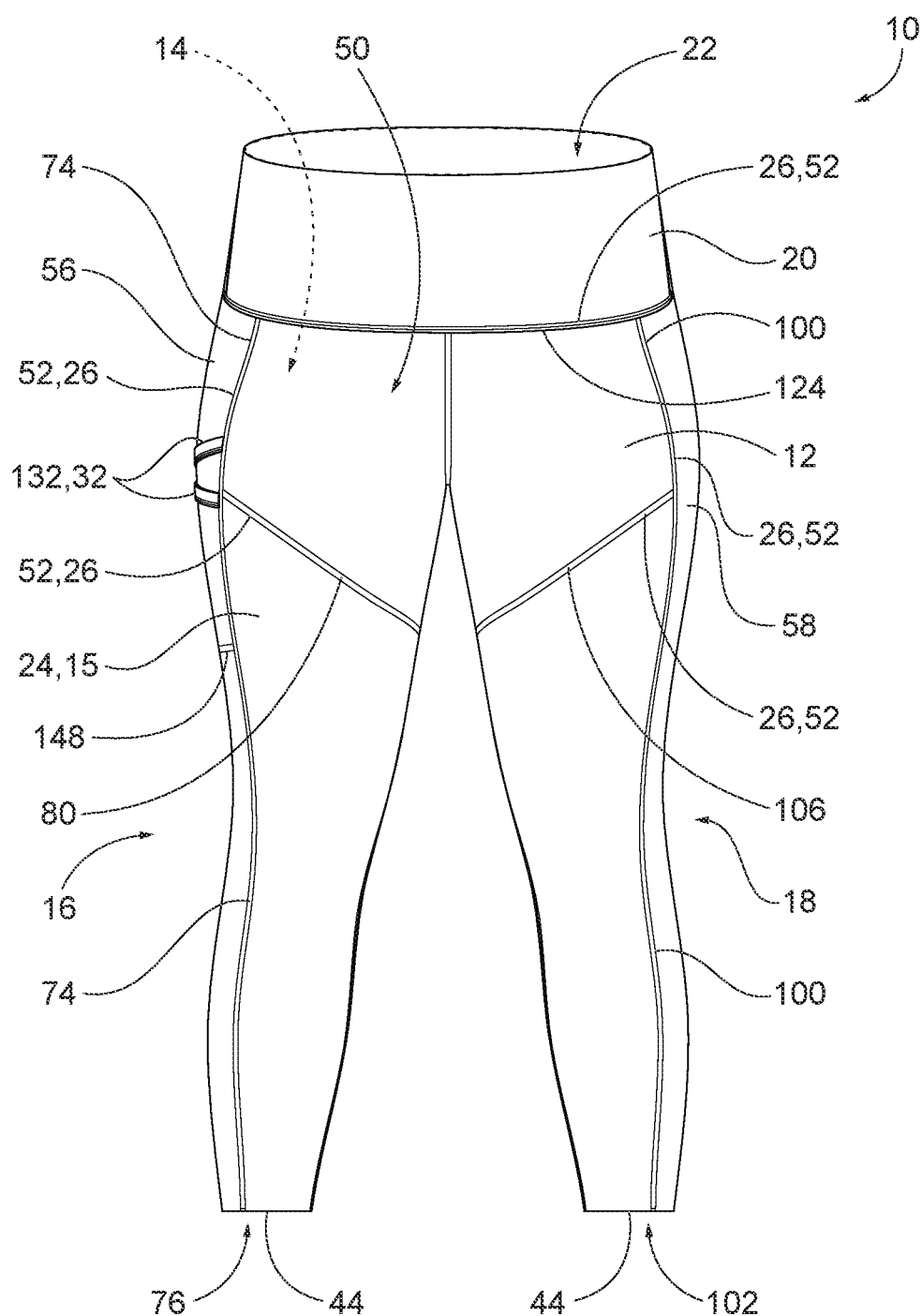
FIG. 7 is a front elevation view of the lower body garment of FIG. 6, shown as-worn.
Figure 8:
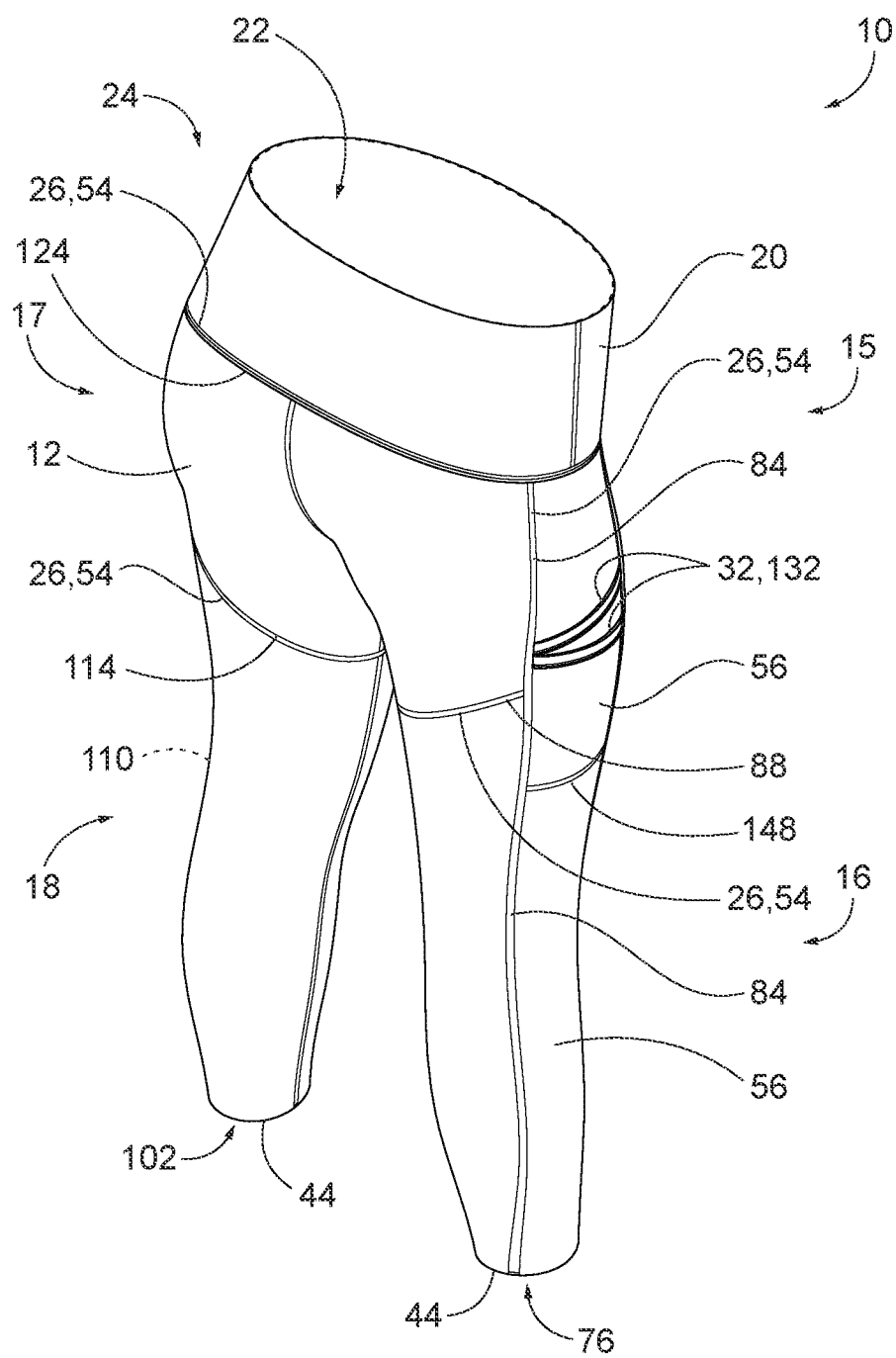
FIG. 8 is a rear perspective view of the lower body garment of FIGS. 6-7, shown as-worn.

Turning now to FIGS. 6-8, illustrative non-exclusive examples of lower body garments 10 are illustrated. Where appropriate, the reference numerals from the schematic illustrations of FIGS. 1-5 are used to designate corresponding parts in FIGS. 6-8; however, the examples of FIGS. 6-8 are non-exclusive and do not limit lower body garments 10 to the illustrated examples of FIGS. 6-8. That is, lower body garments 10 are not limited to the specific examples illustrated in FIGS. 6-8 and may incorporate any number of the various aspects, configurations, characteristics, properties, etc. of lower body garments 10 that are illustrated in and discussed with reference to the schematic representations of FIGS. 1-5 and/or the examples of FIGS. 6-8, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again with respect to FIGS. 6-8; however, it is within the scope of the present disclosure that the previously discussed features, variants, etc. may be utilized therewith.

FIGS. 6-8 show an example of lower body garment 10 in the form of leggings, or tights, though as disclosed throughout, lower body garments 10 may be any desired length. All of FIGS. 6-8 illustrate the example of lower body garment 10 shown in an as-worn configuration (e.g., "inflated" as if donned by a wearer), with FIG. 6 showing a side view of lower body garment 10, FIG. 7 showing a front view, and FIG. 8 showing a rear perspective view.

As best seen in FIGS. 7-8, peripheral lining perimeter 26 is present and visible on exterior side 24 of examples of lower body garments 10, and may coincide with right and left anterior angled seams 80, 106, right and left posterior angled seams 88, 114, a portion of right and left anterior vertically extending seams 74, 100, a portion of right and left posterior vertically extending seams 84, 110, and inferior edge seam 124 of waistband portion 20. In other words, external seams of lower body garments 10 (e.g., seams 80, 106, 88, 114, 74, 100, 84, and 110, or at least a portion thereof) may coextend with, or coincide with internal seams of peripheral lining perimeter 26, along which interior lining 14 is coupled to interior side 22 of lower body garment 10. Thus, seams 80, 106, 88, 114, 74, 100, 84, and 110 of peripheral lining perimeter 26 may extend through all layers of lower body garment 10 (e.g., through interior lining 14 and main body 12). Right and left anterior angled seams 80, 106, right and left posterior angled seams 88, 114, right and left anterior vertically extending seams 74, 100, right and left posterior vertically extending seams 84, 110, and inferior edge seam 124 of waistband portion 20 may be formed of flatlock stitching, or other low profile or minimally visible stitching or bonding technique. These external seams on exterior side 24 are configured to look like design elements of lower body garments 10, and do not give the appearance of briefs, underwear, or gussets. On the other hand, fluid retention gusset 28 may be coupled to interior lining 14 along seams along gusset perimeter 30 that are not coupled to main body 12, and thus not visible on exterior side 24 of lower body garments 10, as shown in FIGS. 6-8.

As noted above in connection with FIG. 2, lower body garments 10 may include one or more pockets 32, which may be positioned anywhere on lower body garment 10, as desired. For example, as shown in FIGS. 6-8, one or more pockets 32 may be positioned on right leg portion 16, left leg portion 18, and/or waistband portion 20. One or more pockets 32 may be positioned on anterior side 15 of lower body garment 10 and/or on posterior side 17 of lower body garment 10. In this example, lower body garment 10 includes one or more pockets 32 in the form of a double pocket 132 that includes at least two partially overlapping pockets 32. Additionally or alternatively, one or more pockets 32 may be mesh pockets (e.g., at least partially formed using a mesh material). As best seen in FIG. 6, pockets 32 may be bounded by right anterior vertically extending seam 74 and right posterior vertically extending seam 84. In other words, one or more pockets 32 may be positioned on or within right lateral leg region 56 of right leg portion 16. Additionally or alternatively, lower body garment 10 may include one or more pockets 32 that are bounded by left anterior vertically extending seam 100 and left posterior vertically extending seam 110. In other words, one or more pockets 32 may be positioned on or within left lateral leg region 58 of left leg portion 18. One or more pockets 32 may be applied to or coupled to exterior surface 24 of main body 12. Additionally or alternatively, one or more pockets 32 may be embedded within or formed in or between one or more layers of main body 12. One or more pockets 32 may be open along a respective top edge 134 of the respective pocket 32, such that items may simply be inserted into the respective pocket 32 by passing the items through the opening at top edge 134. Additionally or alternatively, one or more pockets 32 may include one or more closures 33 (FIG. 2) such as hook-and-loop closures, zippers, snaps, buttons, magnets, and/or overlapping layers of fabric that are configured to prevent items from falling out of the pockets 32.

In various examples of lower body garments 10, pockets 32 may include side pockets formed along one or both lateral sides of lower body garment 10, front pockets formed on anterior side 15 of lower body garment 10, and/or rear pockets formed on posterior side 17 of lower body garment 10. One or more pockets 32 may be formed of one or more additional layers of material applied to right leg portion 16, left leg portion 18, and/or waistband portion 20 to form pockets 32. Pockets 32 may be formed on exterior side 24 of lower body garment 10 and/or on interior side 22 of lower body garment 10. Pockets 32 may be smaller sized, such as to securely hold a key or card, and/or may be larger, such as to hold a mobile phone. In some examples, lower body garment 10 may have an inferior pocket seam 148 that serves to bound, or provide the lower expanse of, pockets 32. In some examples, one or more inferior pocket seams 148 may be visible on exterior side 24 of lower body garments 10, such as within right lateral leg region 56 and/or left lateral leg region 58. The example of FIGS. 6-8 shows one inferior pocket seam 148 within right lateral leg region 56, though lower body garments 10 are not limited to the same. For example, inferior pocket seams 148 additionally or alternatively may be placed within waistband portion 20, on posterior side 17, on anterior side 15, on right leg portion 16, and/or on left leg portion 18.

Figure 9:
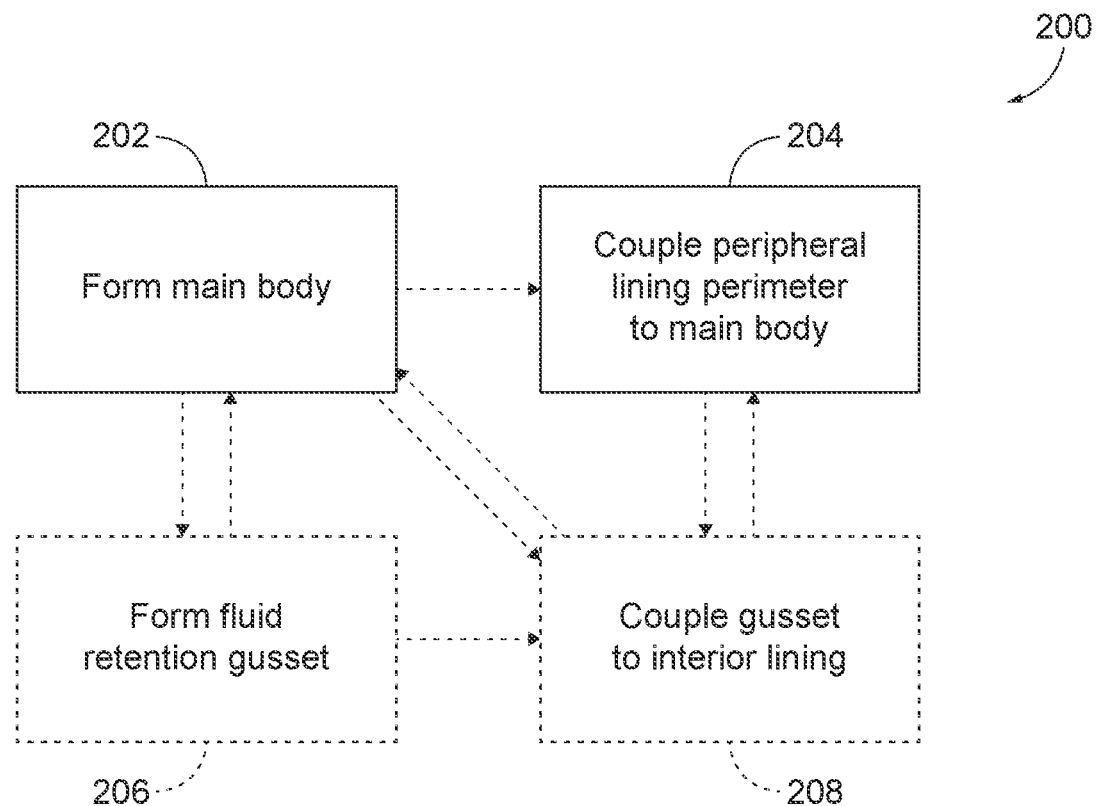
FIG. 9 is a schematic flowchart diagram depicting examples of methods of manufacturing a lower body garment according to the present disclosure.

FIG. 9 schematically provides a flowchart that represents illustrative, non-exclusive examples of methods 200 according to the present disclosure. In FIG. 9, some steps are illustrated in dashed boxes indicating that such steps may be optional or may correspond to an optional version of a method 200 according to the present disclosure. That said, not all methods 200 according to the present disclosure are required to include the steps illustrated in solid boxes. The methods 200 and steps illustrated in FIG. 9 are not limiting and other methods and steps are within the scope of the present disclosure, including methods having greater than or fewer than the number of steps illustrated, as understood from the discussions herein.

Methods 200 of making lower body garments 10 according to the present disclosure generally include forming a main body (e.g., main body 12), at 202, and coupling a peripheral lining perimeter of an interior lining (e.g., peripheral lining perimeter 26 of interior lining 14) to the main body at 204, such that the interior lining is positioned adjacent the interior side of the main body. The main body of disclosed methods 200 may include any of the features of examples of lower body garments 10 disclosed herein, and generally includes forming a main body having a right leg portion, a left leg portion, a waistband portion, an interior side that faces the wearer when the lower body garment is worn, and an exterior side that faces outwardly away from the wearer when the lower body garment is worn.

Methods 200 optionally may include forming a fluid retention gusset (e.g., fluid retention gusset 28), at 206. Said fluid retention gusset formed at 206 may include a moisture-wicking layer configured to be positioned against the wearer when the lower body garment is worn, an absorbent layer configured to absorb and retain at least 1 teaspoon (5 ml) of liquid, and a moisture-impermeable layer coupled to the moisture-wicking layer such that the absorbent layer is sandwiched between the moisture-wicking layer and the moisture-impermeable layer. The fluid retention gusset may be secured with respect to the main body such that the moisture-impermeable layer is positioned with respect to the main body such that the fluid retention gusset is configured to substantially prevent liquid from leaving the fluid retention gusset to the exterior side of the main body. To this end, methods 200 may include coupling a gusset perimeter of the fluid retention gusset (e.g., gusset perimeter 30) to the interior lining, at 208, such that the interior lining 14 positions the fluid retention gusset with respect to the main body once the interior lining is coupled to the main body along the peripheral lining perimeter at 204. Coupling the gusset perimeter to the interior lining at 208 and coupling the interior lining to the main body at 204 may be performed such that the interior lining is positioned adjacent the interior side of the main body and such that the interior lining surrounds the gusset perimeter. In this manner, the fluid retention gusset 28 may be secured with respect to the main body without being directly coupled to the main body. In some methods 200, the interior lining is coupled to the main body at 204 such that a right lateral leg region and a left lateral leg region separate an anterior perimeter portion of the peripheral lining perimeter from a posterior perimeter portion of the peripheral lining perimeter, thereby creating a coupling where the interior lining does not extend all the way around the circumference of the wearer's legs due to this discontinuity on the lateral leg regions of the lower body garment.

Illustrative, non-exclusive examples of inventive subject matter according to the present disclosure are described in the following enumerated paragraphs:

A1. A lower body garment configured to be worn by a wearer, the lower body garment comprising:
  a main body comprising a right leg portion, a left leg portion, and a waistband portion, wherein the main body comprises an interior side that faces the wearer when the lower body garment is worn, and wherein the main body further comprises an exterior side that faces outwardly away from the wearer when the lower body garment is worn; and
  an interior lining positioned adjacent the interior side of the main body, wherein the interior lining comprises a peripheral lining perimeter that is coupled to the main body.

A1.1. The lower body garment of paragraph A1, further comprising a fluid retention gusset configured to retain at least 1 teaspoon (5 ml) of fluid excreted from the wearer such that the fluid is at least substantially prevented from exiting the fluid retention gusset to the exterior side of the main body.

A1.2. The lower body garment of paragraph A1 or A1.1, comprising a/the fluid retention gusset, wherein the fluid retention gusset comprises:
  a moisture-wicking layer configured to be positioned against the wearer when the lower body garment is worn;
  an absorbent layer configured to absorb and retain at least 1 teaspoon (5 ml) of liquid; and
  a moisture-impermeable layer coupled to the moisture-wicking layer such that the absorbent layer is sandwiched between the moisture-wicking layer and the moisture-impermeable layer, wherein the moisture-impermeable layer is positioned with respect to the main body such that the moisture-impermeable layer separates the absorbent layer from the exterior side of the main body.

A1.3. The lower body garment of paragraph A1.1 or A1.2, wherein the fluid retention gusset is integrally formed with the interior lining.

A1.4. The lower body garment of any of paragraphs A1.1-A1.3, wherein the interior lining surrounds and is coupled to a gusset perimeter of the fluid retention gusset.

A1.5. The lower body garment of any of paragraphs A1.1-A1.4, wherein the interior lining is configured to secure the fluid retention gusset with respect to the main body such that the fluid retention gusset is not directly coupled to the main body.

A.1.6. The lower body garment of any of paragraphs A1.1-A1.5, wherein the fluid retention gusset is not directly coupled to the main body A2. The lower body garment of any of paragraphs A1-A1.6, wherein the interior lining comprises a right lining portion and a left lining portion.

A3. The lower body garment of paragraph A2, wherein the right lining portion comprises a right anterior portion positioned on an anterior side of the lower body garment, and wherein the right lining portion further comprises a right posterior portion positioned on a posterior side of the lower body garment.

A4. The lower body garment of paragraph A3, wherein the right anterior portion joins the right posterior portion along a right inseam of the lower body garment.

A5. The lower body garment of any of paragraphs A3-A4, wherein a right upper edge of the right anterior portion joins the waistband portion of the lower body garment.

A6. The lower body garment of any of paragraphs A3-A5, wherein a right lateral edge of the right anterior portion joins a right lateral leg region of the right leg portion of the main body along a right anterior vertically extending seam present on both the interior side and the exterior side of the main body.

A7. The lower body garment of paragraph A6, wherein the right anterior vertically extending seam extends from the waistband portion to or towards a right leg opening at an inferior end of the right leg portion.

A8. The lower body garment of any of paragraphs A3-A7, wherein a right lower edge of the right anterior portion extends obliquely between a/the right inseam and a/the right anterior vertically extending seam.

A8.1. The lower body garment of paragraph A8, wherein the right lower edge of the right anterior portion defines a right anterior angled seam present on both the interior side and the exterior side of the main body.

A9. The lower body garment of any of paragraphs A3-A8.1, wherein a right lateral edge of the right posterior portion joins a/the right lateral leg region of the right leg portion of the main body along a right posterior vertically extending seam present on both the interior side and the exterior side of the main body.

A10. The lower body garment of paragraph A9, wherein the right posterior vertically extending seam extends from the waistband portion to or towards a/the right leg opening at an/the inferior end of the right leg portion.

A11. The lower body garment of any of paragraphs A3-A10, wherein a right lower edge of the right posterior portion extends obliquely between a/the right inseam and a/the right posterior vertically extending seam.

A11.1. The lower body garment of paragraph A11, wherein the right lower edge of the right posterior portion defines a right posterior angled seam present on both the interior side and the exterior side of the main body.

A12. The lower body garment of any of paragraphs A2-A11.1, wherein the left lining portion comprises a left anterior portion positioned on an/the anterior side of the lower body garment, and wherein the left lining portion further comprises a left posterior portion positioned on a/the posterior side of the lower body garment.

A13. The lower body garment of paragraph A12, wherein the left anterior portion joins the left posterior portion along a left inseam of the lower body garment.

A14. The lower body garment of any of paragraphs A12-A13, wherein a left upper edge of the left anterior portion joins the waistband portion of the lower body garment.

A15. The lower body garment of any of paragraphs A12-A14, wherein a left lateral edge of the left anterior portion joins a left lateral leg region of the left leg portion of the main body along a left anterior vertically extending seam present on both the interior side and the exterior side of the main body.

A16. The lower body garment of paragraph A15, wherein the left anterior vertically extending seam extends from the waistband portion to or towards a left leg opening at an inferior end of the left leg portion.

A17. The lower body garment of any of paragraphs A12-A16, wherein a left lower edge of the left anterior portion extends obliquely between a/the left inseam and a/the left anterior vertically extending seam.

A17.1. The lower body garment of paragraph A17, wherein the left lower edge of the left anterior portion defines a left anterior angled seam present on both the interior side and the exterior side of the main body.

A18. The lower body garment of any of paragraphs A12-A17.1, wherein a left lateral edge of the left posterior portion joins a/the left lateral leg region of the left leg portion of the main body along a left posterior vertically extending seam present on both the interior side and the exterior side of the main body.

A19. The lower body garment of paragraph A18, wherein the left posterior vertically extending seam extends from the waistband portion to or towards a/the left leg opening at an/the inferior end of the left leg portion.

A20. The lower body garment of any of paragraphs A12-A19, wherein a left lower edge of the left posterior portion extends obliquely between a/the left inseam and a/the left posterior vertically extending seam.

A20.1. The lower body garment of paragraph A20, wherein the left lower edge of the left posterior portion defines a left posterior angled seam present on both the interior side and the exterior side of the main body.

A21. The lower body garment of any of paragraphs A1-A20.1, wherein the interior lining further comprises a superior anterior portion, wherein the superior anterior portion joins the waistband portion, an anterior superior edge of a/the fluid retention gusset, a/the right anterior portion of the interior lining, and a/the left anterior portion of the interior lining.

A22. The lower body garment of paragraph A21, wherein the superior anterior portion extends laterally to at least partially underlie both the right leg portion and the left leg portion.

A23. The lower body garment of any of paragraphs A1-A22, wherein the interior lining further comprises a superior posterior portion, wherein the superior posterior portion joins the waistband portion, a posterior superior edge of a/the fluid retention gusset, a/the right posterior portion of the interior lining, and a/the left posterior portion of the interior lining.

A24. The lower body garment of any of paragraphs A1-A23, wherein a/the superior posterior portion joins a/the right posterior vertically extending seam and a/the left posterior vertically extending seam, wherein the right posterior vertically extending seam and the left posterior vertically extending seam are present on both the interior side and the exterior side of the main body.

A25. The lower body garment of paragraph A23 or A24, wherein the superior posterior portion extends laterally to at least partially underlie both the right leg portion and the left leg portion.

A26. The lower body garment of any of paragraphs A1-A25, wherein the peripheral lining perimeter is present on the exterior side of the main body.

A26.1. The lower body garment of any of paragraphs A1-A26, wherein the peripheral lining perimeter comprises flatlock stitching.

A27. The lower body garment of any of paragraphs A1-A26.1, wherein the peripheral lining perimeter is at least partly defined by and/or coincides with a/the right upper edge of a/the right anterior portion of the interior lining, a/the left upper edge of a/the left anterior portion of the interior lining, at least part of a/the right anterior vertically extending seam, at least part of a/the left anterior vertically extending seam, at least part of a/the right posterior vertically extending seam, at least part of a/the left posterior vertically extending seam, a/the left posterior angled seam, a/the left anterior angled seam, a/the right anterior angled seam, and/or a/the right posterior angled seam.

A28. The lower body garment of any of paragraphs A1-A27, wherein the peripheral lining perimeter is partly defined by and/or coincides with an inferior edge seam of the waistband portion along an/the anterior side of the lower body garment and along a/the posterior side of the lower body garment.

A29. The lower body garment of any of paragraphs A1-A28, wherein a/the fluid retention gusset integrally formed with the interior lining is shaped and sized such that it is configured to capture blood and urine exiting the wearer's pelvic region while the lower body garment is worn.

A30. The lower body garment of any of paragraphs A1-A29, wherein the interior lining is configured to maintain positioning of a/the fluid retention gusset while the lower body garment is worn, and wherein the exterior side of the lower body garment is devoid of seams along the gusset perimeter.

A30.1. The lower body garment of any of paragraphs A1-A30, wherein the interior lining is coupled to the gusset perimeter via flatlock stitching that is not attached to the main body and not present on the exterior side of the lower body garment.

A31. The lower body garment of any of paragraphs A1-A30.1, wherein the interior lining comprises mesh.

A32. The lower body garment of any of paragraphs A1-A31, further comprising one or more pockets.

A33. The lower body garment of paragraph A32, wherein the one or more pockets comprises a double pocket comprising at least two partially overlapping pockets.

A34. The lower body garment of any of paragraphs A32-A33, wherein the one or more pockets comprises one or more mesh pockets.

A35. The lower body garment of any of paragraphs A32-A34, wherein the one or more pockets are bounded by a/the right anterior vertically extending seam and a/the right posterior vertically extending seam.

A36. The lower body garment of any of paragraphs A32-A35, wherein the one or more pockets are bounded by a/the left anterior vertically extending seam and a/the left posterior vertically extending seam.

A37. The lower body garment of any of paragraphs A32-A36, wherein the one or more pockets comprise a closure.

A38. The lower body garment of any of paragraphs A32-A37, wherein the one or more pockets are open along a respective top edge of each of the one or more pockets.

A39. The lower body garment of any of paragraphs A32-A38, comprising one or more pockets positioned on a/the left lateral leg region of the left leg portion.

A40. The lower body garment of any of paragraphs A32-A39, comprising one or more pockets positioned on a/the right lateral leg region of the right leg portion.

A41. The lower body garment of any of paragraphs A1-A40, wherein the lower body garment comprises shorts, tights, capris, or leggings.

A42. The lower body garment of any of paragraphs A1-A41, wherein a/the moisture-wicking layer of a/the fluid retention gusset integrally formed with the interior lining comprises cotton, carbon cotton, and/or carbon cotton spandex.

A43. The lower body garment of any of paragraphs A1-A42, wherein a/the moisture-wicking layer of a/the fluid retention gusset integrally formed with the interior lining is configured to be quick-drying, odor fighting, and/or antimicrobial.

A44. The lower body garment of any of paragraphs A1-A43, wherein a/the moisture-impermeable layer of a/the fluid retention gusset integrally formed with the interior lining is positioned such that it contacts the main body of the lower body garment when the lower body garment is worn, such that the moisture-impermeable layer separates an/the absorbent layer of the fluid retention gusset from the exterior side of the main body of the lower body garment.

A45. The lower body garment of any of paragraphs A1-A44, wherein a/the fluid retention gusset integrally formed with the interior lining is configured to be leakproof.

A46. The lower body garment of any of paragraphs A1-A45, wherein an/the absorbent layer of a/the fluid retention gusset integrally formed with the interior lining comprises polyester nylon.

A47. The lower body garment of any of paragraphs A1-A45, wherein a/the absorbent layer of a/the fluid retention gusset integrally formed with the interior lining absorbs at least 2 teaspoons (10 ml), at least 3 teaspoons (15 ml), at least 4 teaspoons (20 ml), and/or at least 5 teaspoons (25 ml) of liquid.

A48. The lower body garment of any of paragraphs A1-A47, wherein a/the moisture-impermeable layer of a/the fluid retention gusset integrally formed with the interior lining comprises a leak resistant or waterproof fabric or other moisture barrier material, a moisture barrier layer, a moisture barrier film, moisture barrier membrane, a waterproof, water-resistant, or water-repellant treatment, and/or a waterproof, water-resistant, or water-repellant coating.

A49. The lower body garment of any of paragraphs A1-A48, wherein the main body comprises a four-way stretch fabric that is lightweight, breathable, quick-drying, wicking, and/or odor-resistant.

A50. The lower body garment of any of paragraphs A1-A49, wherein the main body comprises nylon and elastane.

A51. The lower body garment of any of paragraphs A1-A50, wherein the lower body garment has an inseam length that is at least 2 inches (5 centimeters (cm)), at least 3 inches (7.5 cm), at least 4 inches (10 cm), at least 5 inches (12.7 cm), at least 6 inches (15.25 cm), at least 7 inches (17.8 cm), at least 8 inches (20 cm), at least 9 inches (22.9 cm), at least 10 inches (25.4 cm), and/or at most 12 inches (30.5 cm).

A52. The lower body garment of any of paragraphs A1-A50, wherein the lower body garment has an inseam length that is at least 15 inches (38 cm), at least 18 inches (45 cm), at least 21 inches (53 cm), at least 24 inches (61 cm), at least 27 inches (68.5 cm), at least 30 inches (76 cm), at least 33 inches (84 cm), and/or at most 36 inches (91 cm).

A53. The lower body garment of any of paragraphs A1-A52, wherein the lower body garment is configured to be worn as an outer garment.

A54. The lower body garment of any of paragraphs A1-A53, wherein the lower body garment is configured to be machine-washable and re-worn numerous times.

A55. The lower body garment of any of paragraphs A1-A54, wherein the waistband portion is seamless.

A56. The lower body garment of any of paragraphs A1-A55, wherein the waistband portion comprises elastic positioned along a superior edge of the waistband portion on the interior side of the lower body garment, and wherein the elastic is bonded to the waistband portion via pin bond mesh glue, bonding tape, and/or silicone bonding glue.

A57. The lower body garment of any of paragraphs A1-A56, wherein a/the fluid retention gusset integrally formed with the interior lining comprises a varying width along a length of the fluid retention gusset, such that a first portion of the fluid retention gusset is narrower than one or more other portions of the fluid retention gusset, wherein the first portion is configured to be positioned at the narrowest part of the wearer's pelvic region when the lower body garment is worn.

A58. The lower body garment of any of paragraphs A1-A57, wherein a/the fluid retention gusset integrally formed with the interior lining has a/the length that is at least 6 inches (15 cm), at least 7 inches (17.8 cm), at least 8 inches (20 cm), at least 9 inches (22.8 cm), at least 10 inches (25.4 cm), at least 11 inches (28 cm), at least 12 inches (30.5 cm), at least 13 inches (33 cm), at least 14 inches (35.5 cm), and/or at most 15 inches (38 cm) long.

A59. The lower body garment of any of paragraphs A1-A58, wherein a/the left leg opening at an/the inferior end of the left leg portion and a/the right leg opening at an/the inferior end of the right leg portion each comprises a seamless flocked trim on the interior side of the main body.

A60. The lower body garment of any of paragraphs A1-A59, wherein a pelvic region of the lower body garment is free of seams on the exterior side of the lower body garment.

A61. The lower body garment of any of paragraphs A1-A60, wherein the right leg portion comprises a/the right lateral leg region, and wherein the left leg portion comprises a/the left lateral leg region.

A61.1. The lower body garment of any of paragraphs A1-A61, wherein a/the left lateral leg region of the left leg portion extends between a/the left anterior vertically extending seam and a/the left posterior vertically extending seam, and wherein a/the right lateral leg region of the right leg portion extends between a/the right anterior vertically extending seam and a/the right posterior vertically extending seam.

A61.2. The lower body garment of any of paragraphs A1-A61.1, wherein a/the right lateral leg region of the right leg portion is bounded on an/the anterior side of the lower body garment by a/the right anterior vertically extending seam, wherein the right lateral leg region is bounded on a/the posterior side of the lower body garment by a/the right posterior vertically extending seam, wherein a/the left lateral leg region of the left leg portion is bounded on the anterior side of the lower body garment by a/the left anterior vertically extending seam, and wherein the left lateral leg region is bounded on the posterior side of the lower body garment by a/the left posterior vertically extending seam.

A62. The lower body garment of any of paragraphs A1-A61.2, wherein a/the right lateral leg region of the right leg portion is positioned laterally to a first vertically extending centerline of the right leg portion.

A63. The lower body garment of any of paragraphs A1-A62, wherein a/the left lateral leg region of the left leg portion is positioned laterally to a second vertically extending centerline of the left leg portion.

A64. The lower body garment of any of paragraphs A1-A63, wherein the peripheral lining perimeter does not traverse, extend across, underlie, overlap with, coextend to or with, or pass into a/the right lateral leg region of the right leg portion or a/the left lateral leg region of the left leg portion.

A65. The lower body garment of any of paragraphs A1-A64, wherein the interior lining is only coupled to the main body along the peripheral lining perimeter, and is otherwise not attached to the main body.

A66. The lower body garment of any of paragraphs A1-A65, wherein the peripheral lining perimeter is discontinuous between an/the anterior side of the lower body garment and a/the posterior side of the lower body garment.

A67. The lower body garment of any of paragraphs A1-A66, wherein the peripheral lining perimeter comprises an anterior perimeter portion and a posterior perimeter portion, wherein a/the right lateral leg region of the right leg portion and a/the left lateral leg region of the left leg portion separate the anterior perimeter portion of the peripheral lining perimeter from the posterior perimeter portion of the peripheral lining perimeter, wherein the anterior perimeter portion is positioned on an/the anterior side of the lower body garment, and wherein the posterior perimeter portion is positioned on a/the posterior side of the lower body garment.

B1. A method of making a lower body garment, the method comprising:
  forming a main body comprising a right leg portion, a left leg portion, and a waistband portion, wherein the main body comprises an interior side that faces the wearer when the lower body garment is worn, and wherein the main body further comprises an exterior side that faces outwardly away from the wearer when the lower body garment is worn; and
  coupling a peripheral lining perimeter of an interior lining to the main body such that the interior lining is positioned adjacent the interior side of the main body.

B2. The method of paragraph B1, further comprising forming a fluid retention gusset, wherein the fluid retention gusset comprises:
  a moisture-wicking layer configured to be positioned against the wearer when the lower body garment is worn;
  an absorbent layer configured to absorb and retain at least 1 teaspoon (5 ml) of liquid; and
  a moisture-impermeable layer coupled to the moisture-wicking layer such that the absorbent layer is sandwiched between the moisture-wicking layer and the moisture-impermeable layer, wherein the moisture-impermeable layer is positioned with respect to the main body such that the fluid retention gusset is configured to substantially prevent liquid from leaving the fluid retention gusset to the exterior side of the main body.

B3. The method of any of paragraphs B1-B2, further comprising coupling the interior lining to a gusset perimeter of a/the fluid retention gusset such that the interior lining is positioned adjacent the interior side of the main body and such that the interior lining surrounds the gusset perimeter, wherein the interior lining is configured to secure the fluid retention gusset with respect to the main body such that the fluid retention gusset is not directly coupled to the main body.

B4. The method of any of paragraphs B1-B3, wherein the right leg portion comprises a right lateral leg region, wherein the right lateral leg region is positioned laterally to a first vertically extending centerline of the right leg portion, wherein the left leg portion comprises a left lateral leg region, wherein the left lateral leg region is positioned laterally to a second vertically extending centerline of the left leg portion, and wherein the coupling the peripheral lining perimeter of the interior lining to the main body comprises coupling the peripheral lining perimeter such that the right lateral leg region and the left lateral leg region separate an anterior perimeter portion of the peripheral lining perimeter from a posterior perimeter portion of the peripheral lining perimeter, wherein the anterior perimeter portion is positioned on an anterior side of the lower body garment, and wherein the posterior perimeter portion is positioned on a posterior side of the lower body garment.

B5. The method of any of paragraphs B1-B4, wherein the lower body garment comprises the lower body garment of any of paragraphs A1-A67.

C1. The use of the lower body garment of any of paragraphs A1-67 to absorb and retain liquid excretions from a wearer of the lower body garment.

As used herein, the terms "selective" and "selectively," when modifying an action, movement, configuration, or other activity of one or more components or characteristics of an apparatus, mean that the specific action, movement, configuration, or other activity is a direct or indirect result of dynamic processes and/or user manipulation of an aspect of, or one or more components of, the apparatus. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one example, to at least one, optionally including more than one, A, with no B present (and optionally including entities other than B); in another example, to at least one, optionally including more than one, B, with no A present (and optionally including entities other than A); in yet another example, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" may mean A alone, B alone, C alone, A and B together, A and C together, B and C together, or A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first direction that is at least substantially parallel to a second direction includes a first direction that is within an angular deviation of 22.5° relative to the second direction and also includes a first direction that is identical to the second direction.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

As used herein, terms such as "coincide," "meet," and "coextensive," as used to describe a relative position of a first edge or seam relative to a second edge or seam, generally refers to a configuration in which the first edge or seam and the second edge or seam are positioned at respective locations that are not spatially separated from one another. However, it is to be understood that a description herein of two or more components meeting, coinciding, or being coextensive does not necessarily mean that the two or more components are exactly and/or precisely aligned with one another. For example, as known in the art, garment construction is not perfect, and the imprecision introduced by human- and/or machine-performed manufacturing can introduce slight misalignments between components that nominally are intended or designed to be aligned with one another. Accordingly, for the purposes of the present disclosure, the terms "coincide," "coextensive," and "meet" are intended to encompass configurations in which the components are perfectly aligned, as well as configurations in which the components are slightly misaligned as a result of manufacturing tolerances.

The invention claimed is:

1. A lower body garment configured to be worn by a wearer, the lower body garment comprising:
    a main body comprising a right leg portion, a left leg portion, and a waistband portion, wherein the main body comprises an interior side that faces the wearer when the lower body garment is worn, wherein the main body further comprises an exterior side that faces outwardly away from the wearer when the lower body garment is worn, wherein the right leg portion comprises a right lateral leg region, wherein the right lateral leg region is positioned laterally to a first vertically extending centerline of the right leg portion, wherein the left leg portion comprises a left lateral leg region, and wherein the left lateral leg region is positioned laterally to a second vertically extending centerline of the left leg portion;
    an interior lining positioned adjacent the interior side of the main body, wherein the interior lining comprises a peripheral lining perimeter, wherein the interior lining is coupled to the main body only along the peripheral lining perimeter, wherein the peripheral lining perimeter comprises an anterior perimeter portion positioned on an anterior side of the lower body garment and a posterior perimeter portion positioned on a posterior side of the lower body garment, wherein the right lateral leg region and the left lateral leg region separate the anterior perimeter portion of the peripheral lining perimeter from the posterior perimeter portion of the peripheral lining perimeter, wherein the interior lining comprises a right lining portion and a left lining portion, wherein the right lining portion comprises a right anterior portion positioned on the anterior side of the lower body garment, wherein the right lining portion further comprises a right posterior portion positioned on the posterior side of the lower body garment, wherein the left lining portion comprises a left anterior portion positioned on the anterior side of the lower body garment, and wherein the left lining portion further comprises a left posterior portion positioned on the posterior side of the lower body garment;
    a right anterior vertically extending seam extending from the waistband portion towards a right leg opening at an inferior end of the right leg portion, wherein the right anterior vertically extending seam is present on both the interior side and the exterior side of the main body;
    a right posterior vertically extending seam extending from the waistband portion towards the right leg opening, wherein the right posterior vertically extending seam is present on both the interior side and the exterior side of the main body, and wherein the right lateral leg region extends between the right anterior vertically extending seam and the right posterior vertically extending seam;
    a left anterior vertically extending seam extending from the waistband portion towards a left leg opening at an inferior end of the left leg portion, wherein the left anterior vertically extending seam is present on both the interior side and the exterior side of the main body; and
    a left posterior vertically extending seam extending from the waistband portion towards the left leg opening, wherein the left posterior vertically extending seam is present on both the interior side and the exterior side of the main body, and wherein the left lateral leg region extends between the left anterior vertically extending seam and the left posterior vertically extending seam.

2. The lower body garment according to claim 1, further comprising a fluid retention gusset configured to retain at least 5 milliliters of fluid excreted from the wearer such that the fluid is at least substantially prevented from exiting the fluid retention gusset to the exterior side of the main body, wherein the interior lining surrounds and is coupled to a gusset perimeter of the fluid retention gusset, and wherein the fluid retention gusset is not directly coupled to the main body.

3. The lower body garment according to claim 1, wherein the right anterior portion joins the right posterior portion along a right inseam of the lower body garment, and wherein the left anterior portion joins the left posterior portion along a left inseam of the lower body garment.

4. The lower body garment according to claim 1, wherein the right anterior vertically extending seam extends inferiorly from the waistband portion to the right leg opening, wherein the right posterior vertically extending seam extends inferiorly from the waistband portion to the right leg opening, wherein the left anterior vertically extending seam extends inferiorly from the waistband portion to the left leg opening, and wherein the left posterior vertically extending seam extends inferiorly from the waistband portion to the left leg opening.

5. The lower body garment according to claim 1, wherein a right lateral edge of the right anterior portion joins the right lateral leg region along the right anterior vertically extending seam, wherein a right lateral edge of the right posterior portion joins the right lateral leg region of the right leg portion of the main body along the right posterior vertically extending seam, wherein a left lateral edge of the left anterior portion joins the left lateral leg region along the left anterior vertically extending seam, and wherein a left lateral edge of the left posterior portion joins the left lateral leg region along the left posterior vertically extending seam.

6. The lower body garment according to claim 1, wherein a right lower edge of the right anterior portion extends obliquely between a right inseam of the lower body garment and the right anterior vertically extending seam, wherein the right lower edge of the right anterior portion defines a right anterior angled seam present on both the interior side and the exterior side of the main body, wherein a right lower edge of the right posterior portion extends obliquely between the right inseam and the right posterior vertically extending seam, wherein the right lower edge of the right posterior portion defines a right posterior angled seam present on both the interior side and the exterior side of the main body, wherein a left lower edge of the left anterior portion extends obliquely between a left inseam of the lower body garment and the left anterior vertically extending seam, wherein the left lower edge of the left anterior portion defines a left anterior angled seam present on both the interior side and the exterior side of the main body, wherein a left lower edge of the left posterior portion extends obliquely between the left inseam and the left posterior vertically extending seam, and wherein the left lower edge of the left posterior portion defines a left posterior angled seam present on both the interior side and the exterior side of the main body.

7. The lower body garment according to claim 1, further comprising at least two partially overlapping pockets, wherein the at least two partially overlapping pockets are bounded by the right anterior vertically extending seam and the right posterior vertically extending seam, and wherein the at least two partially overlapping pockets are open along a respective top edge of each of the at least two partially overlapping pockets.

8. The lower body garment according to claim 1, wherein the interior lining further comprises:
a superior anterior portion, wherein the superior anterior portion joins the waistband portion, the right anterior portion of the interior lining, and the left anterior portion of the interior lining; and
a superior posterior portion, wherein the superior posterior portion joins the waistband portion, the right posterior portion of the interior lining, and the left posterior portion of the interior lining.

9. The lower body garment according to claim 1, wherein the peripheral lining perimeter is at least partly defined by a right upper edge of a right anterior portion of the interior lining, a left upper edge of a left anterior portion of the interior lining, at least part of a right anterior vertically extending seam, at least part of a left anterior vertically extending seam, at least part of a right posterior vertically extending seam, at least part of a left posterior vertically extending seam, a left posterior angled seam, a left anterior angled seam, a right anterior angled seam, and a right posterior angled seam.

10. The lower body garment according to claim 9, wherein the peripheral lining perimeter is partly defined by an inferior edge seam of the waistband portion along an anterior side of the lower body garment and along a posterior side of the lower body garment.

11. The lower body garment according to claim 1, wherein the interior lining comprises mesh.

12. The lower body garment according to claim 1, wherein the lower body garment is configured to be worn as an outer garment.

13. The lower body garment according to claim 1, wherein the lower body garment is configured to be machine-washable and re-worn numerous times.

14. A lower body garment configured to be worn by a wearer, the lower body garment comprising:
a main body comprising a right leg portion, a left leg portion, and a waistband portion, wherein the main body comprises an interior side that faces the wearer when the lower body garment is worn, and wherein the main body further comprises an exterior side that faces outwardly away from the wearer when the lower body garment is worn;
a fluid retention gusset configured to retain at least 5 milliliters of fluid excreted from the wearer such that the fluid is at least substantially prevented from exiting the fluid retention gusset to the exterior side of the main body, the fluid retention gusset comprising:
a moisture-wicking layer configured to be positioned against the wearer when the lower body garment is worn;
an absorbent layer configured to absorb and retain at least 5 milliliters of liquid; and
a moisture-impermeable layer coupled to the moisture-wicking layer such that the absorbent layer is sandwiched between the moisture-wicking layer and the moisture-impermeable layer, wherein the moisture-impermeable layer is positioned with respect to the main body such that the moisture-impermeable layer separates the absorbent layer from the exterior side of the main body; and
an interior lining positioned adjacent the interior side of the main body, wherein the interior lining surrounds and is coupled to a gusset perimeter of the fluid retention gusset, wherein the interior lining is configured to secure the fluid retention gusset with respect to the main body such that the fluid retention gusset is not directly coupled to the main body, and wherein the interior lining comprises a peripheral lining perimeter that is coupled to the main body.

15. The lower body garment according to claim 14, wherein the peripheral lining perimeter is present on the exterior side of the main body, wherein the interior lining is configured to maintain positioning of the fluid retention gusset while the lower body garment is worn, and wherein the exterior side of the lower body garment is devoid of seams along the gusset perimeter.

16. The lower body garment according to claim 14, wherein the fluid retention gusset is shaped and sized such that it is configured to capture blood and urine exiting a pelvic region of the wearer while the lower body garment is worn.

17. The lower body garment according to claim 14, wherein the interior lining is coupled to the gusset perimeter via flatlock stitching that is not attached to the main body and not present on the exterior side of the lower body garment.

18. A method of making the lower body garment of claim 1, the method comprising:
forming the main body; and
coupling the peripheral lining perimeter of the interior lining to the main body, such that the interior lining is positioned adjacent the interior side of the main body, and such that the right lateral leg region and the left lateral leg region separate the anterior perimeter portion of the peripheral lining perimeter from the posterior perimeter portion of the peripheral lining perimeter.

19. The lower body garment according to claim 1, wherein the right leg portion, the left leg portion, and the waistband portion of the main body are continuous with one another, such that the main body extends across the anterior side of the lower body garment and the posterior side of the lower body garment.

20. A lower body garment configured to be worn by a wearer, the lower body garment comprising:
a main body comprising a right leg portion, a left leg portion, and a waistband portion, wherein the main body comprises an interior side that faces the wearer when the lower body garment is worn, wherein the main body further comprises an exterior side that faces outwardly away from the wearer when the lower body garment is worn, wherein the right leg portion comprises a right lateral leg region, wherein the right lateral leg region is positioned laterally to a first vertically extending centerline of the right leg portion, wherein the left leg portion comprises a left lateral leg region, and wherein the left lateral leg region is positioned laterally to a second vertically extending centerline of the left leg portion;

an interior lining positioned adjacent the interior side of the main body, wherein the interior lining comprises a peripheral lining perimeter that is coupled to the main body, wherein the peripheral lining perimeter comprises an anterior perimeter portion positioned on an anterior side of the lower body garment and a posterior perimeter portion positioned on a posterior side of the lower body garment, and wherein the right lateral leg region and the left lateral leg region separate the anterior perimeter portion of the peripheral lining perimeter from the posterior perimeter portion of the peripheral lining perimeter; and a fluid retention gusset having a gusset perimeter, wherein the interior lining surrounds and is coupled to the gusset perimeter, wherein the fluid retention gusset is not directly coupled to the main body, and wherein the fluid retention gusset comprises:

an absorbent layer configured to absorb and retain at least 5 milliliters of liquid excreted from the wearer; and a moisture-impermeable layer coupled positioned with respect to the main body such that the moisture-impermeable layer separates the absorbent layer from the main body.

21. A lower body garment configured to be worn by a wearer, the lower body garment comprising:

a main body comprising a right leg portion, a left leg portion, and a waistband portion, wherein the main body comprises an interior side that faces the wearer when the lower body garment is worn, wherein the main body further comprises an exterior side that faces outwardly away from the wearer when the lower body garment is worn, wherein the right leg portion comprises a right lateral leg region, wherein the right lateral leg region is positioned laterally to a first vertically extending centerline of the right leg portion, wherein the left leg portion comprises a left lateral leg region, and wherein the left lateral leg region is positioned laterally to a second vertically extending centerline of the left leg portion; and an interior lining positioned adjacent the interior side of the main body, wherein the interior lining comprises a peripheral lining perimeter, wherein the interior lining is coupled to the main body only along the peripheral lining perimeter, wherein the peripheral lining perimeter comprises an anterior perimeter portion positioned on an anterior side of the lower body garment and a posterior perimeter portion positioned on a posterior side of the lower body garment, and wherein the right lateral leg region and the left lateral leg region separate the anterior perimeter portion of the peripheral lining perimeter from the posterior perimeter portion of the peripheral lining perimeter, wherein the interior lining comprises a right lining portion and a left lining portion, wherein the right lining portion comprises a right anterior portion positioned on the anterior side of the lower body garment, wherein the right lining portion further comprises a right posterior portion positioned on the posterior side of the lower body garment, wherein the left lining portion comprises a left anterior portion positioned on the anterior side of the lower body garment, wherein the left lining portion further comprises a left posterior portion positioned on the posterior side of the lower body garment, wherein the right anterior portion joins the right posterior portion along a right inseam of the lower body garment, and wherein the left anterior portion joins the left posterior portion along a left inseam of the lower body garment.

22. A lower body garment configured to be worn by a wearer, the lower body garment comprising:

a main body comprising a right leg portion, a left leg portion, and a waistband portion, wherein the main body comprises an interior side that faces the wearer when the lower body garment is worn, wherein the main body further comprises an exterior side that faces outwardly away from the wearer when the lower body garment is worn, wherein the right leg portion comprises a right lateral leg region, wherein the right lateral leg region is positioned laterally to a first vertically extending centerline of the right leg portion, wherein the left leg portion comprises a left lateral leg region, and wherein the left lateral leg region is positioned laterally to a second vertically extending centerline of the left leg portion; and an interior lining positioned adjacent the interior side of the main body, wherein the interior lining comprises a peripheral lining perimeter, wherein the interior lining is coupled to the main body only along the peripheral lining perimeter, wherein the peripheral lining perimeter comprises an anterior perimeter portion positioned on an anterior side of the lower body garment and a posterior perimeter portion positioned on a posterior side of the lower body garment, wherein the right lateral leg region and the left lateral leg region separate the anterior perimeter portion of the peripheral lining perimeter from the posterior perimeter portion of the peripheral lining perimeter, and wherein the peripheral lining perimeter is at least partly defined by a right upper edge of a right anterior portion of the interior lining, a left upper edge of a left anterior portion of the interior lining, at least part of a right anterior vertically extending seam, at least part of a left anterior vertically extending seam, at least part of a right posterior vertically extending seam, at least part of a left posterior vertically extending seam, a left posterior angled seam, a left anterior angled seam, a right anterior angled seam, and a right posterior angled seam.

\* \* \* \* \*